(12) United States Patent
Zhang

(10) Patent No.: US 10,188,867 B2
(45) Date of Patent: Jan. 29, 2019

(54) METHOD AND APPARATUS FOR BEAT ACQUISITION DURING TEMPLATE GENERATION IN A MEDICAL DEVICE HAVING DUAL SENSING VECTORS

(71) Applicant: Medtronic, Inc., Minneapolis, MN (US)

(72) Inventor: Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 76 days.

(21) Appl. No.: 14/604,260

(22) Filed: Jan. 23, 2015

(65) Prior Publication Data

US 2016/0213941 A1 Jul. 28, 2016

(51) Int. Cl.
| | |
|---|---|
| *A61N 1/39* | (2006.01) |
| *A61B 5/0452* | (2006.01) |
| *A61N 1/37* | (2006.01) |
| *A61B 5/00* | (2006.01) |
| *A61N 1/362* | (2006.01) |
| *A61N 1/365* | (2006.01) |

(52) U.S. Cl.
CPC ........ *A61N 1/3987* (2013.01); *A61B 5/04525* (2013.01); *A61B 5/686* (2013.01); *A61B 5/6869* (2013.01); *A61B 5/7221* (2013.01); *A61B 5/7264* (2013.01); *A61N 1/3624* (2013.01); *A61N 1/3702* (2013.01); *A61N 1/3956* (2013.01); *A61N 1/3622* (2013.01); *A61N 1/36507* (2013.01)

(58) Field of Classification Search
CPC .. A61N 1/3987; A61N 1/3622; A61N 1/3624; A61N 1/36507; A61N 1/3702; A61N 1/3956; A61B 5/04525; A61B 5/686; A61B 5/6869; A61B 5/7221; A61B 5/7264
USPC ...................................... 607/7, 60
See application file for complete search history.

(56) References Cited

U.S. PATENT DOCUMENTS

| | | | |
|---|---|---|---|
| 4,721,114 A | 1/1988 | DuFault et al. | |
| 4,870,974 A | 10/1989 | Wang | |
| 5,191,884 A | 3/1993 | Gilli et al. | |
| 5,312,443 A | 5/1994 | Adams et al. | |

(Continued)

FOREIGN PATENT DOCUMENTS

WO     01/80042 A1     10/2001

OTHER PUBLICATIONS (PCT/US2016/014227) PCT Notification of Transmittal of the International Search Report and the Written Opinion of the International Searching Authority, dated Mar. 31, 2016, 11 pages.

(Continued)

*Primary Examiner* — Michael Carey

(57) ABSTRACT

A method and medical device for generating a template that includes sensing a cardiac signal from a plurality of electrodes, determining a plurality of beats in response to the sensed cardiac signal, determining whether to store a beat of the plurality of beats in a subgroup of a plurality of subgroups for storing beats, determining whether a number of beats stored in one of the plurality of subgroups exceeds a subgroup threshold, and generating a template in response to beats stored in the one of the plurality of subgroups that exceeds the subgroup threshold.

20 Claims, 15 Drawing Sheets

(56) References Cited

U.S. PATENT DOCUMENTS

| | | | |
|---|---|---|---|
| 5,312,445 A | 5/1994 | Nappholz et al. | |
| 5,334,966 A | 8/1994 | Takeshima et al. | |
| 5,458,623 A | 10/1995 | Lu et al. | |
| 5,474,574 A * | 12/1995 | Payne | A61N 1/3931 607/7 |
| 5,687,733 A | 11/1997 | McKown | |
| 5,720,295 A | 2/1998 | Greenhut et al. | |
| 5,755,739 A | 5/1998 | Sun et al. | |
| 5,817,134 A | 10/1998 | Greenhut et al. | |
| 6,134,479 A | 10/2000 | Brewer et al. | |
| 6,230,059 B1 * | 5/2001 | Duffin | A61B 5/0008 607/60 |
| 6,287,328 B1 | 9/2001 | Snyder et al. | |
| 6,304,773 B1 | 10/2001 | Taylor et al. | |
| 6,397,100 B2 | 5/2002 | Stadler et al. | |
| 6,449,503 B1 | 9/2002 | Hsu | |
| 6,470,210 B1 * | 10/2002 | Chen | A61N 1/3962 600/515 |
| 6,516,225 B1 | 2/2003 | Florio | |
| 6,745,068 B2 | 6/2004 | Koyrakh et al. | |
| 6,892,094 B2 | 5/2005 | Ousdigian et al. | |
| 6,895,272 B2 | 5/2005 | Seim et al. | |
| 6,904,315 B2 | 6/2005 | Panken et al. | |
| 6,904,319 B2 | 6/2005 | Seim et al. | |
| 6,912,418 B1 | 6/2005 | Florio | |
| 6,922,584 B2 | 7/2005 | Wang et al. | |
| 7,010,347 B2 | 3/2006 | Schecter | |
| 7,103,464 B2 | 9/2006 | Zielke | |
| 7,184,815 B2 | 2/2007 | Kim et al. | |
| 7,187,965 B2 | 3/2007 | Bischoff et al. | |
| 7,242,978 B2 | 7/2007 | Cao et al. | |
| 7,308,308 B1 | 12/2007 | Xi et al. | |
| 7,499,751 B2 | 3/2009 | Meyer et al. | |
| 7,509,160 B2 | 3/2009 | Bischoff et al. | |
| 7,515,956 B2 | 4/2009 | Thompson | |
| 7,561,911 B2 | 7/2009 | Cao et al. | |
| 7,596,405 B2 | 9/2009 | Kurzweil et al. | |
| 7,640,054 B2 | 12/2009 | Koyrakh et al. | |
| 7,657,307 B2 | 2/2010 | Van Dam et al. | |
| 7,706,869 B2 | 4/2010 | Cao et al. | |
| 7,729,754 B2 | 6/2010 | Cao et al. | |
| 7,734,333 B2 | 6/2010 | Ghanem et al. | |
| 7,734,336 B2 | 6/2010 | Ghanem et al. | |
| 7,742,812 B2 | 6/2010 | Ghanem et al. | |
| 7,761,142 B2 | 7/2010 | Ghanem et al. | |
| 7,761,150 B2 | 7/2010 | Ghanem et al. | |
| 7,769,452 B2 | 8/2010 | Ghanem et al. | |
| 7,774,616 B2 | 8/2010 | Dale et al. | |
| 7,826,893 B2 | 11/2010 | Cao et al. | |
| 7,904,153 B2 | 3/2011 | Greenhut et al. | |
| 7,907,993 B2 | 3/2011 | Ghanem et al. | |
| 7,937,135 B2 | 5/2011 | Ghanem et al. | |
| 7,941,214 B2 | 5/2011 | Kleckner et al. | |
| 7,983,742 B2 | 7/2011 | Starc | |
| 7,991,471 B2 | 8/2011 | Ghanem et al. | |
| 8,000,778 B2 | 8/2011 | Seim et al. | |
| 8,068,901 B2 | 11/2011 | Ghanem et al. | |
| 8,095,206 B2 | 1/2012 | Ghanem et al. | |
| 8,160,684 B2 | 4/2012 | Ghanem et al. | |
| 8,195,280 B2 | 6/2012 | Van Dam et al. | |
| 8,306,618 B2 | 11/2012 | Ghanem et al. | |
| 8,412,316 B2 | 4/2013 | Seim et al. | |
| 8,428,697 B2 | 4/2013 | Zhang et al. | |
| 8,428,705 B2 | 4/2013 | Kurzweil et al. | |
| 8,435,185 B2 | 5/2013 | Ghanem et al. | |
| 8,521,268 B2 | 8/2013 | Zhang et al. | |
| 8,548,573 B2 | 10/2013 | Keefe | |
| 8,560,058 B2 | 10/2013 | Babaeizadeh et al. | |
| 8,588,895 B2 | 11/2013 | Sanghera et al. | |
| 2002/0058878 A1 | 5/2002 | Kohler et al. | |
| 2002/0165459 A1 | 11/2002 | Starobin et al. | |
| 2002/0193695 A1 * | 12/2002 | Koyrakh | A61B 5/04525 600/510 |
| 2003/0023178 A1 | 1/2003 | Bischoff et al. | |
| 2003/0083587 A1 | 5/2003 | Ferek-Petric | |
| 2003/0120312 A1 | 6/2003 | Cammilli et al. | |
| 2004/0021523 A1 | 2/2004 | Sadowy et al. | |
| 2004/0030256 A1 | 2/2004 | Lin | |
| 2004/0049120 A1 | 3/2004 | Cao et al. | |
| 2004/0059237 A1 | 3/2004 | Narayan et al. | |
| 2004/0093037 A1 | 5/2004 | Henry | |
| 2004/0254613 A1 | 12/2004 | Ostroff et al. | |
| 2005/0065564 A1 | 3/2005 | Seim et al. | |
| 2005/0149125 A1 | 7/2005 | Kim et al. | |
| 2005/0234358 A1 | 10/2005 | Cao et al. | |
| 2006/0042809 A1 | 3/2006 | Neufeld et al. | |
| 2006/0074332 A1 | 4/2006 | Bischoff et al. | |
| 2006/0079797 A1 | 4/2006 | Bischoff et al. | |
| 2006/0079798 A1 | 4/2006 | Bischoff et al. | |
| 2006/0106323 A1 | 5/2006 | Bischoff et al. | |
| 2006/0111747 A1 | 5/2006 | Cazares et al. | |
| 2006/0217621 A1 | 9/2006 | Kim et al. | |
| 2007/0142736 A1 | 6/2007 | Cazares et al. | |
| 2007/0232948 A1 | 10/2007 | Stadler et al. | |
| 2007/0233198 A1 | 10/2007 | Ghanem et al. | |
| 2007/0270704 A1 | 11/2007 | Ghanem et al. | |
| 2008/0132965 A1 * | 6/2008 | Ostroff | A61N 1/3956 607/14 |
| 2008/0140143 A1 | 6/2008 | Ettori et al. | |
| 2011/0301661 A1 | 12/2011 | Seim et al. | |
| 2012/0172942 A1 | 7/2012 | Berg | |

OTHER PUBLICATIONS (PCT/US2016/014261) PCT Notification of Transmittal of the International Search Report and the Written Opinion of the International Searching Authority, dated Apr. 7, 2016, 10 pages.

"P-wave evidence as a method for improving algorithm to detect atrial fibrillation in insertable cardiac monitors", Helmut Purerfellner, MD. FHRS, et al., 2014 Heart Rhythm Society, vol. 11, No. 9, Sep. 2014, pp. 1575-1583.

* cited by examiner

__US 10,188,867 B2__

METHOD AND APPARATUS FOR BEAT ACQUISITION DURING TEMPLATE GENERATION IN A MEDICAL DEVICE HAVING DUAL SENSING VECTORS

RELATED APPLICATION

Cross-reference is hereby made to commonly assigned U.S. patent application Ser. No. 14/604,111, filed on even date herewith entitled "METHOD AND APPARATUS FOR BEAT ACQUISITION DURING TEMPLATE GENERATION IN A MEDICAL DEVICE HAVING DUAL SENSING VECTORS", and incorporated by reference in its entirety.

TECHNICAL FIELD

The disclosure relates generally to implantable medical devices and, in particular, to an apparatus and method for acquiring beats utilized for cardiac event template generation in a medical device.

BACKGROUND

Implantable medical devices are available for treating cardiac tachyarrhythmias by delivering anti-tachycardia pacing therapies and electrical shock therapies for cardioverting or defibrillating the heart. Such a device, commonly known as an implantable cardioverter defibrillator or "ICD", senses electrical activity from the heart, determines a patient's heart rate, and classifies the rate according to a number of heart rate zones in order to detect episodes of ventricular tachycardia or fibrillation. Typically a number of rate zones are defined according to programmable detection interval ranges for detecting slow ventricular tachycardia, fast ventricular tachycardia and ventricular fibrillation. Intervals between sensed R-waves, corresponding to the depolarization of the ventricles, are measured. Sensed R-R intervals falling into defined detection interval ranges are counted to provide a count of ventricular tachycardia (VT) or ventricular fibrillation (VF) intervals, for example. A programmable number of intervals to detect (NID) defines the number of tachycardia intervals occurring consecutively or out of a given number of preceding event intervals that are required to detect VT or VF.

Tachyarrhythmia detection may begin with detecting a fast ventricular rate, referred to as rate- or interval-based detection. Once VT or VF is detected based on rate, the morphology of the sensed depolarization signals, e.g. wave shape, amplitude or other features, may be used in discriminating heart rhythms to improve the sensitivity and specificity of tachyarrhythmia detection methods.

A primary goal of a tachycardia detection algorithm is to rapidly respond to a potentially malignant rhythm with a therapy that will terminate the arrhythmia with high certainty. Another goal, however, is to avoid excessive use of ICD battery charge, which shortens the life of the ICD, e.g. due to delivering unnecessary therapies or therapies at a higher voltage than needed to terminate a detected tachyarrhythmia. Minimizing the patient's exposure to painful shock therapies is also an important consideration. Accordingly, a need remains for ICDs that perform tachycardia discrimination with high specificity and control therapy delivery to successfully terminate a detected VT requiring therapy while conserving battery charge and limiting patient exposure to delivered shock therapy by withholding therapy delivery whenever possible in situations where the therapy may not be required.

DETAILED DESCRIPTION

Figure 1:
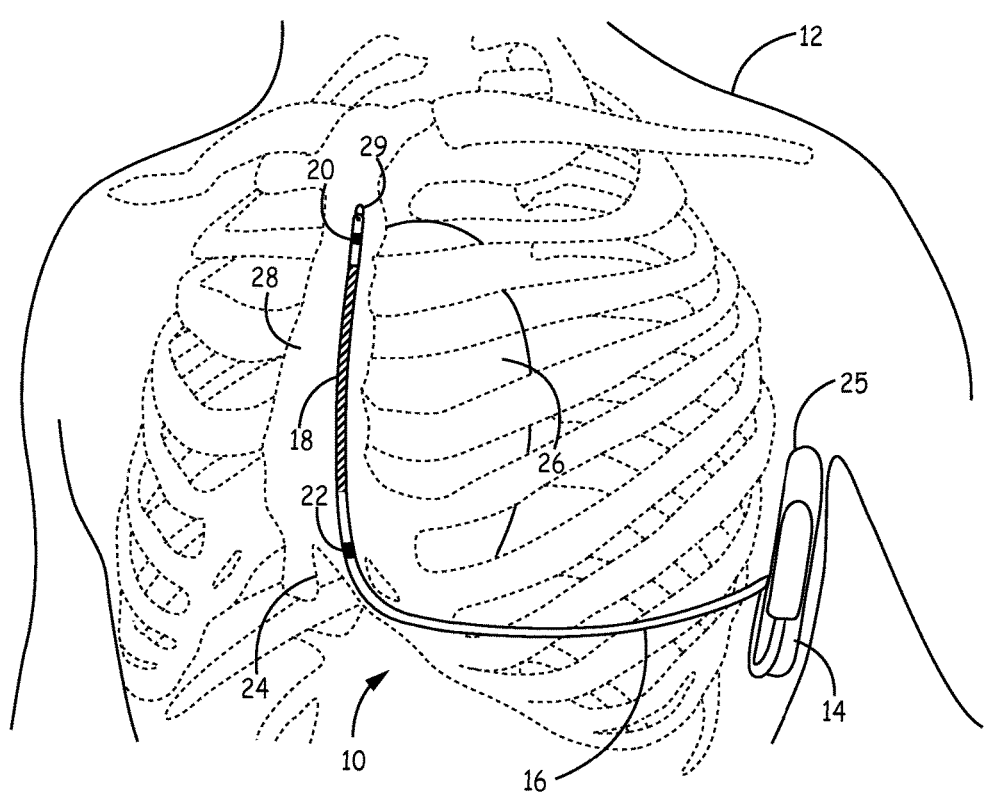
FIG. 1 is a conceptual diagram of a patient implanted with an example extravascular cardiac defibrillation system.

FIG. 1 is a conceptual diagram of a patient 12 implanted with an example extravascular cardiac defibrillation system 10. In the example illustrated in FIG. 1, extravascular cardiac defibrillation system 10 is an implanted subcutaneous ICD system. However, the techniques of this disclosure may also be utilized with other extravascular implanted cardiac defibrillation systems, such as a cardiac defibrillation system having a lead implanted at least partially in a substernal or submuscular location. Additionally, the techniques of this disclosure may also be utilized with other implantable systems, such as implantable pacing systems, implantable neurostimulation systems, drug delivery systems, automatic external defibrillators (AED) or other systems in which leads, catheters or other components are implanted at extravascular locations within patient 12. This disclosure, however, is described in the context of an implantable extravascular cardiac defibrillation system for purposes of illustration.

Extravascular cardiac defibrillation system 10 includes an implantable cardioverter defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24, defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

Defibrillation lead 16 is placed along sternum 28 such that a therapy vector between defibrillation electrode 18 and a second electrode (such as a housing or can 25 of ICD 14 or an electrode placed on a second lead) is substantially across the ventricle of heart 26. The therapy vector may, in one example, be viewed as a line that extends from a point on the defibrillation electrode 18 to a point on the housing or can 25 of ICD 14. In another example, defibrillation lead 16 may be placed along sternum 28 such that a therapy vector between defibrillation electrode 18 and the housing or can 25 of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or more centrally located over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 18, 20, and 22, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing or can 25 that forms a hermetic seal that protects components within ICD 14. The housing 25 of ICD 14 may be formed of a conductive material, such as titanium or other biocompatible conductive material or a combination of conductive and non-conductive materials. In some instances, the housing 25 of ICD 14 functions as an electrode (referred to as a housing electrode or can electrode) that is used in combination with one of electrodes 18, 20, or 22 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. Housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 18, 20, and 22. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 18, 20 and 22, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 18, 20 and 22. In other words, each of the one or more elongated electrical conductors contained within the lead body of defibrillation lead 16 may engage with respective ones of electrodes 18, 20 and 22. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 18, 20 and 22 and transmit sensed electrical signals from one or more of electrodes 18, 20 and 22 to the sensing module within ICD 14.

ICD 14 may sense electrical activity of heart 26 via one or more sensing vectors that include combinations of electrodes 20 and 22 and the housing or can 25 of ICD 14. For example, ICD 14 may obtain electrical signals sensed using a sensing vector between electrodes 20 and 22, obtain electrical signals sensed using a sensing vector between electrode 20 and the conductive housing or can 25 of ICD 14, obtain electrical signals sensed using a sensing vector between electrode 22 and the conductive housing or can 25 of ICD 14, or a combination thereof. In some instances, ICD 14 may sense cardiac electrical signals using a sensing vector that includes defibrillation electrode 18, such as a sensing vector between defibrillation electrode 18 and one of electrodes 20 or 22, or a sensing vector between defibrillation electrode 18 and the housing or can 25 of ICD 14.

ICD may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 18 of defibrillation lead 16 and the housing or can 25. Defibrillation electrode 18 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 20 and 22 and/or the housing or can 25. Electrodes 20 and 22 may comprise ring electrodes, hemispherical electrodes, coil electrodes, helix electrodes, segmented electrodes, directional electrodes, or other types of electrodes, or combination thereof. Electrodes 20 and 22 may be the same type of electrodes or different types of electrodes, although in the example of FIG. 1 both electrodes 20 and 22 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 22 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum 28. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the sub-xiphoid or inferior xiphoid area, near the apex of the heart, or other location not in direct contact with heart 26 and not subcutaneous. In still further instances, the lead may be implanted at a pericardial or epicardial location outside of the heart 26.

Figure 2:
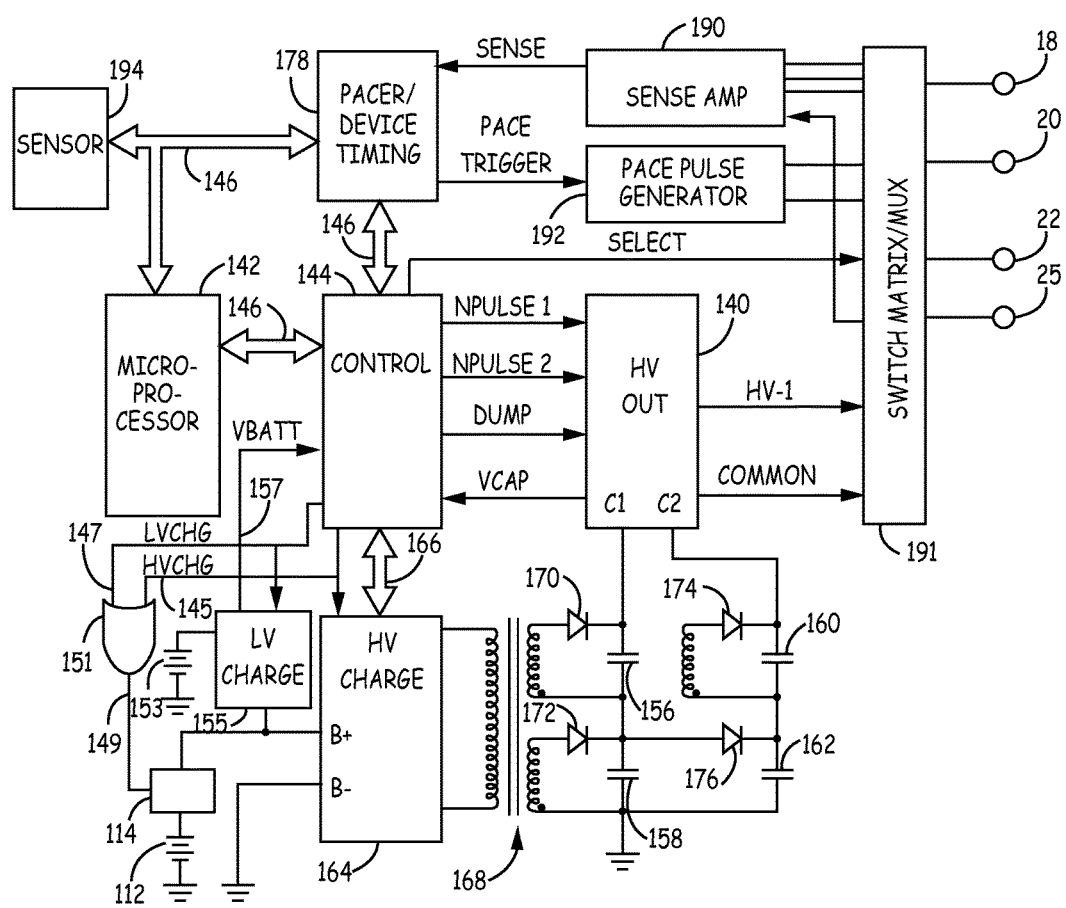
FIG. 2 is an exemplary schematic diagram of electronic circuitry within a hermetically sealed housing of a subcutaneous device according to an embodiment of the present invention.

FIG. 2 is an exemplary schematic diagram of electronic circuitry within a hermetically sealed housing of a subcutaneous device according to an embodiment of the present invention. As illustrated in FIG. 2, subcutaneous device 14 includes a low voltage battery 153 coupled to a power supply (not shown) that supplies power to the circuitry of the subcutaneous device 14 and the pacing output capacitors to supply pacing energy in a manner well known in the art. The low voltage battery 153 may be formed of one or two conventional $LiCF_x$, $LiMnO_2$ or $LiI_2$ cells, for example. The subcutaneous device 14 also includes a high voltage battery 112 that may be formed of one or two conventional LiSVO or $LiMnO_2$ cells. Although two both low voltage battery and a high voltage battery are shown in FIG. 2, according to an embodiment of the present invention, the device 14 could utilize a single battery for both high and low voltage uses.

Further referring to FIG. 2, subcutaneous device 14 functions are controlled by means of software, firmware and hardware that cooperatively monitor the ECG signal, determine when a cardioversion-defibrillation shock or pacing is necessary, and deliver prescribed cardioversion-defibrillation and pacing therapies. The subcutaneous device 14 may incorporate circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks typically employing ICD IPG housing electrodes 28 coupled to the COMMON output 123 of high voltage output circuit 140 and cardioversion-defibrillation electrode 24 disposed posteriorly and subcutaneously and coupled to the HVI output 113 of the high voltage output circuit 140.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The subcutaneous device 14 of the present invention uses maximum voltages in the range of about 300 to approximately 1000 Volts and is associated with energies of approximately 25 to 150 joules or more. The total high voltage capacitance could range from about 50 to about 300 microfarads. Such cardioversion-defibrillation shocks are only delivered when a malignant tachyarrhythmia, e.g., ventricular fibrillation is detected through processing of the far field cardiac ECG employing the detection algorithms as described herein below.

In FIG. 2, sense amp 190 in conjunction with pacer/device timing circuit 178 processes the far field ECG sense signal that is developed across a particular ECG sense vector defined by a selected pair of the subcutaneous electrodes 18, 20, 22 and the can or housing 25 of the device 14, or, optionally, a virtual signal (i.e., a mathematical combination of two vectors) if selected. The selection of the sensing electrode pair is made through the switch matrix/MUX 191 in a manner to provide the most reliable sensing of the ECG signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the Control circuit 144 as a function of the intervals between R-wave sense event signals that are output from the pacer/device timing 178 and sense amplifier circuit 190 to the timing and control circuit 144. It should be noted that the present invention utilizes not only interval based signal analysis method but also supplemental sensors and morphology processing method and apparatus as described herein below.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the subcutaneous device pocket or, alternatively, located on the lead 18 to enable the sensing of contacting or near-contacting tissue oxygenation or color.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a preprogrammed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 300-1000V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 may be charged, for example, by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 18 and 25 coupled to the HV-1 and COMMON output as shown in FIG. 2.

Thus, subcutaneous device 14 monitors the patient's cardiac status and initiates the delivery of a cardioversion-defibrillation shock through the cardioversion-defibrillation electrodes 18 and 25 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. The subcutaneous device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated ICD.

Subcutaneous device 14 desirably includes telemetry circuit (not shown in FIG. 2), so that it is capable of being programmed by means of external programmer 20 via a 2-way telemetry link (not shown). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn.

Various telemetry systems for providing the necessary communications channels between an external programming unit and an implanted device have been developed and are well known in the art. Telemetry systems believed to be suitable for the purposes of practicing the present invention are disclosed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

According to an embodiment of the present invention, in order to automatically select the preferred ECG vector set, it is necessary to have an index of merit upon which to rate the quality of the signal. "Quality" is defined as the signal's ability to provide accurate heart rate estimation and accurate morphological waveform separation between the patient's usual sinus rhythm and the patient's ventricular tachyarrhythmia.

Appropriate indices may include R-wave amplitude, R-wave peak amplitude to waveform amplitude between R-waves (i.e., signal to noise ratio), low slope content, relative high versus low frequency power, mean frequency estimation, probability density function, or some combination of these metrics.

Automatic vector selection might be done at implantation or periodically (daily, weekly, monthly) or both. At implant, automatic vector selection may be initiated as part of an automatic device turn-on procedure that performs such activities as measure lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG vector quality is adequate for the current patient and for the device and lead position, prior to suturing the subcutaneous device 14 device in place and closing the incision. Such an ECG quality indicator would allow the implanting physician to maneuver the device to a new location or orientation to improve the quality of the ECG signals as required. The preferred ECG vector or vectors may also be selected at implant as part of the device turn-on procedure. The preferred vectors might be those vectors with the indices that maximize rate estimation and detection accuracy. There may also be an a priori set of vectors that are preferred by the physician, and as long as those vectors exceed some minimum threshold, or are only slightly worse than some other more desirable vectors, the a priori preferred vectors are chosen. Certain vectors may be considered nearly identical such that they are not tested unless the a priori selected vector index falls below some predetermined threshold.

Depending upon metric power consumption and power requirements of the device, the ECG signal quality metric may be measured on the range of vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the subcutaneous device 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep (using an internal clock (e.g., 2:00 am) or, alternatively, infer sleep by determining the patient's position (via a 2- or 3-axis accelerometer) and a lack of activity).

If infrequent automatic, periodic measurements are made, it may also be desirable to measure noise (e.g., muscle, motion, EMI, etc.) in the signal and postpone the vector selection measurement when the noise has subsided.

Subcutaneous device 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture.

In the preferred embodiment, vector quality metric calculations would occur a number of times over approximately 1 minute, once per day, for each vector. These values would be averaged for each vector over the course of one week. Averaging may consist of a moving average or recursive average depending on time weighting and memory considerations. In this example, the preferred vector(s) would be selected once per week.

Figure 3:
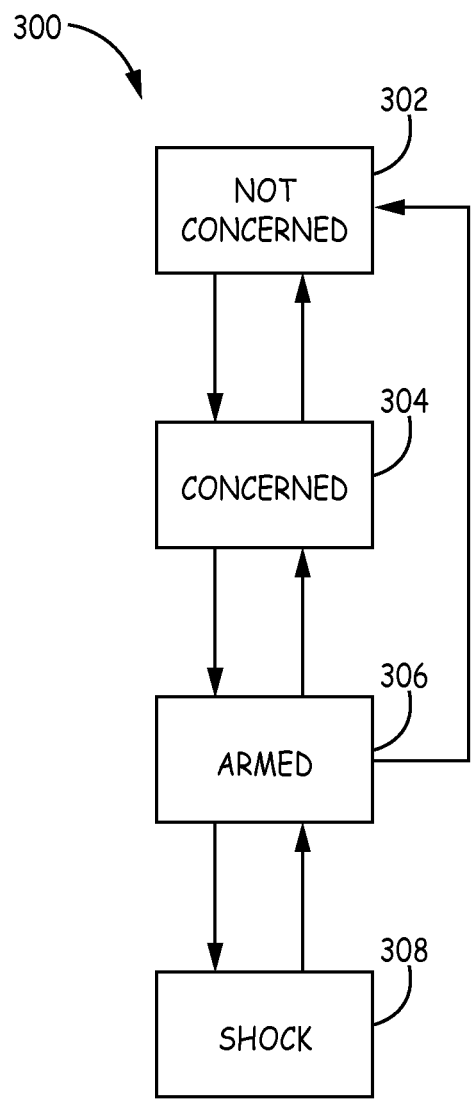
FIG. 3 is a state diagram of detection of arrhythmias in a medical device according to an embodiment of the present invention.

FIG. 3 is a state diagram of detection of arrhythmias in a medical device according to an embodiment of the present invention. As illustrated in FIG. 3, during normal operation, the device 14 is in a not concerned state 302, during which R-wave intervals are being evaluated to identify periods of rapid rates and/or the presence of asystole. Upon detection of short R-wave intervals simultaneously in two separate ECG sensing vectors, indicative of an event that, if confirmed, may require the delivery of therapy, the device 14 transitions from the not concerned state 302 to a concerned state 304. In the concerned state 304 the device 14 evaluates a predetermined window of ECG signals to determine the likelihood that the signal is corrupted with noise and to discriminate rhythms requiring shock therapy from those that do not require shock therapy, using a combination of R-wave intervals and ECG signal morphology information.

If a rhythm requiring shock therapy continues to be detected while in the concerned state 304, the device 14 transitions from the concerned state 304 to an armed state 306. If a rhythm requiring shock therapy is no longer detected while the device is in the concerned state 304 and the R-wave intervals are determined to no longer be short, the device 14 returns to the not concerned state 302. However, if a rhythm requiring shock therapy is no longer detected while the device is in the concerned state 304, but the R-wave intervals continue to be detected as being short, processing continues in the concerned state 304.

In the armed state 306, the device 14 charges the high voltage shocking capacitors and continues to monitor R-wave intervals and ECG signal morphology for spontaneous termination. If spontaneous termination of the rhythm requiring shock therapy occurs, the device 14 returns to the not concerned state 302. If the rhythm requiring shock therapy is still determined to be occurring once the charging of the capacitors is completed, the device 14 transitions from the armed state 306 to a shock state 308. In the shock state 308, the device 14 delivers a shock and returns to the armed state 306 to evaluate the success of the therapy delivered.

The transitioning between the not concerned state 302, the concerned state 304, the armed state 306 and the shock state 308 may be performed as described in detail in U.S. Pat. No. 7,894,894 to Stadler et al., incorporated herein by reference in it's entirety.

Figure 4:
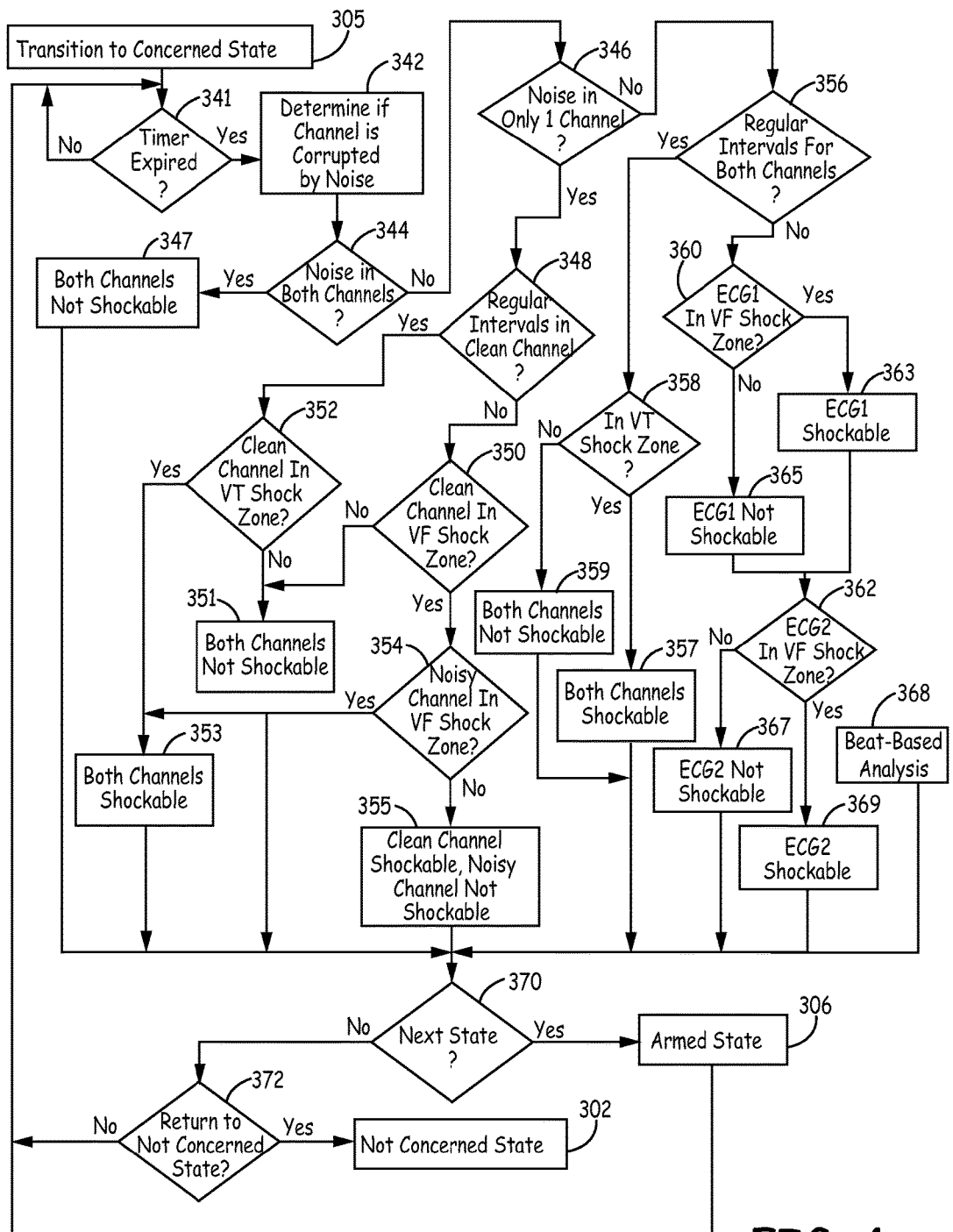
FIG. 4 is a flowchart of a method for detecting arrhythmias in a subcutaneous device according to an embodiment of the present disclosure.

FIG. 4 is a flowchart of a method for detecting arrhythmias in a subcutaneous device according to an embodiment of the present disclosure. As illustrated in FIG. 4, device 14 continuously evaluates the two channels ECG1 and ECG2 associated with two predetermined electrode vectors to determine when sensed events occur. For example, the electrode vectors for the two channels ECG1 and ECG2 may include a first vector (ECG1) selected between electrode 20 positioned on lead 16 and the housing or can 25 of ICD 14, while the other electrode vector (ECG 2) is a vertical electrode vector between electrode 20 and electrode 22 positioned along the lead 16. However, the two sensing channels may in any combination of possible vectors, including those formed by the electrodes shown in FIG. 2, or other additional electrodes (not shown) that may be included along the lead or positioned along the housing of ICD 14.

According to an embodiment of the present application, for example, the device 14 determines whether to transition from the not concerned state 302 to the concerned state 304 by determining a heart rate estimate in response to the sensing of R-waves, as described in U.S. Pat. No. 7,894,894 to Stadler et al., incorporated herein by reference in it's entirety.

Upon transition from the not concerned state to the concerned state, Block 305, a most recent window of ECG data from both channels ECG1 and ECG2 are utilized, such as three seconds, for example, so that processing is triggered in the concerned state 304 by a three-second timeout, rather than by the sensing of an R-wave, which is utilized when in the not concerned state 302. It is understood that while the processing is described as being triggered over a three second period, other times periods for the processing time utilized when in the concerned state 304 may be chosen, but should preferably be within a range of 0.5 to 10 seconds. As a result, although sensing of individual R-waves continues to occur in both channels ECG1 and ECG2 when in the concerned state 304, and the buffer of 12 R-R intervals continues to be updated, the opportunities for changing from the concerned state 304 to another state and the estimates of heart rate only occur once the three-second timer expires. Upon initial entry to the concerned state 304, it is advantageous to process the most recent three-seconds of ECG data, i.e., ECG data for the three seconds leading up to the transition to the concerned state 304. This requires a continuous circular buffering of the most recent three seconds of ECG data even while in the not concerned state 302.

While in the concerned state 304, the present invention determines how sinusoidal and how noisy the signals are in order to determine the likelihood that a ventricular fibrillation (VF) or fast ventricular tachycardia (VT) event is taking place, since the more sinusoidal and low noise the signal is, the more likely a VT/VF event is taking place. As illustrated in FIG. 4, once the device transitions from the not concerned state 302 to the concerned state 304, Block 305, a buffer for each of the two channels ECG 1 and ECG2 for storing classifications of 3-second segments of data as "shockable" or "non-shockable" is cleared. Processing of signals of the two channels ECG1 and ECG2 while in the concerned state 304 is then triggered by the three second time period, rather than by the sensing of an R-wave utilized during the not concerned state 302.

Once the three second time interval has expired, YES in Block 341, morphology characteristics of the signal during the three second time interval for each channel are utilized to determine whether the signals are likely corrupted by noise artifacts and to characterize the morphology of the signal as "shockable" or "not shockable". For example, using the signals associated with the three second time interval, a determination is made for each channel ECG1 and ECG 2 as to whether the channel is likely corrupted by noise, Block 342, and a determination is then made as to whether both channels ECG1 and ECG2 are corrupted by noise, Block 344. According to one embodiment, for example, the device makes the noise determination in Block 344 as described in U.S. patent application Ser. No. 14/255,159 to Zhang, incorporated herein by reference in it's entirety.

Upon determining whether the channels ECG1 and ECG2 are corrupted by noise is made, Block 342, a determination is made as to whether both channels are determined to be noise corrupted, Block 344. If the signal associated with both channels ECG1 and ECG2 is determined to likely be corrupted by noise, both channels are classified as being not shockable, Block 347, and therefore a buffer for each channel ECG1 and ECG 2 containing the last three classifications of the channel is updated accordingly and the process is repeated for the next three-second windows. If both channels ECG1 and ECG2 are not determined to be likely corrupted by noise, No in Block 344, the device distinguishes between either one of the channels being not corrupted by noise or both channels being not corrupted by noise by determining whether noise was determined to be likely in only one of the two channels ECG1 and ECG2, Block 346.

If noise was likely in only one of the two channels, a determination is made whether the signal for the channel not corrupted by noise, i.e., the clean channel, is more likely associated with a VT event or with a VF event by determining, for example, whether the signal for that channel includes R-R intervals that are regular and the channel can be therefore classified as being relatively stable, Block 348. If the R-R intervals are determined not to be relatively stable, NO in Block 348, the signal for that channel is identified as likely being associated with VF, which is then verified by determining whether the signal is in a VF shock zone, Block 350, described below. If R-R intervals for that channel are determined to be stable, YES in Block 348, the signal is identified as likely being associated with VT, which is then verified by determining whether the signal is in a VT shock zone, Block 352, described below.

If noise was not likely for both of the channels, No in Block 346, i.e., both channels are determined to be clean channels, a determination is made whether the signal for both channels is more likely associated with a VT event or with a VF event by determining whether the signal for both channels includes R-R intervals that are regular and can be therefore classified as being relatively stable, Block 356. The determination in Block 356 of whether the R-R intervals are determined to be relatively stable may be made using the method described in U.S. Pat. No. 7,894,894 to Stadler et al., incorporated herein by reference in it's entirety. If the R-R intervals are determined not to be relatively stable, NO in Block 356, the signal for both channels is identified as likely being associated with VF, which is then verified by determining whether the signal for each channel is in a VF shock zone, Block 360, described below. If R-R intervals for both channels are determined to be stable, YES in Block 356, the signal is identified as likely being associated with VT, which is then verified by determining, based on both channels, whether the signal is in a VT shock zone, Block 358.

A VF shock zone is defined for each channel ECG1 and ECG2 based on the relationship between the calculated low slope content and the spectral width associated with the channel, as described in U.S. patent application Ser. No. 14/255,159 to Zhang, incorporated herein by reference in it's entirety.

A determination is made for each channel ECG1 and ECG2 as to whether the low slope content for that channel is less than both the first boundary 502 and the spectral width is less than the second boundary 504, i.e., the low slope content is less than −0.0013×spectral width+0.415, and the spectral width is less than 200. For example, once the event is determined to be associated with VF, i.e., the intervals for both channels are determined to be irregular, No in Block 356, a determination is made that channel ECG1 is in the VF shock zone, Yes in Block 360, if, for channel ECG1, both the low slope content is less than the first boundary 502 and the spectral width is less than the second boundary 504. The three second segment for that channel ECG1 is then determined to be shockable, Block 363 and the associated buffer for that channel is updated accordingly. If either the low slope content for the channel is not less than the first boundary 502 or the spectral width is not less than the second boundary, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, both the low slope content is less than the first boundary 502 and the spectral width is less than the second boundary 504. The three second segment for that channel ECG2 is then determined to be shockable, Block 369 and the associated buffer for that channel is updated accordingly. If either the low slope content for the channel is not less than the first boundary 502 or the spectral width is not less than the second boundary, the channel ECG2 is determined not to be in the VF shock zone, No in Block 362, the three second segment for that channel ECG2 is then determined to be not shockable, Block 367, and the associated buffer is updated accordingly.

During the determination of whether the event is within the VT shock zone, Block 358 of FIG. 4, the low slope content and the spectral width is determined for each channel ECG1 and ECG2, as described above in reference to determining the VF shock zone. A determination is made as to which channel of the two signal channels ECG1 and ECG2 contains the minimum low slope content and which channel of the two signal channels ECG 1 and ECG2 contains the minimum spectral width. A first VT shock zone is defined based on the relationship between the low slope content associated with the channel determined to have the minimum low slope content and the spectral width associated with the channel determined to have the minimum spectral width.

As described, during both the VF shock zone test, Blocks 360 and 362, and the VT shock zone test, Block 358, the test results for each channel ECG1 and ECG2 as being classified as shockable or not shockable are stored in a rolling buffer containing the most recent eight such designations, for example, for each of the two channels ECG1 and ECG2 that is utilized in the determination of Block 356, as described below.

If only one of the two channels ECG1 and ECG2 is determined to be corrupted by noise, Yes in Block 346, a determination is made whether the signal for the channel not corrupted by noise, i.e., the "clean channel", is more likely associated with a VT event or with a VF event by determining whether the signal for the clean channel includes R-R intervals that are regular and can be therefore classified as being relatively stable, Block 348. If the R-R intervals are determined not to be relatively stable, NO in Block 348, the signal for the clean channel is identified as likely being associated with VF, which is then verified by determining whether the signal for the clean channel is in a VF shock zone, Block 350, described below. If R-R intervals for the clean channel are determined to be stable, YES in Block 348, the signal is identified as likely being associated with VT, which is then verified by determining whether the signal for the clean channel is in a VT shock zone, Block 352.

According to an embodiment of the present invention, in order to determine whether the signal for the clean channel includes R-R intervals that are regular and the clean channel can be therefore classified as being either relatively stable, Yes in Block 348, or relatively unstable, No in Block 348, the device discriminates VT events from VF events in Block 348 by determining whether the relative level of variation in the RR-intervals associated with the clean channel is regular, as described in U.S. patent application Ser. No. 14/255,159 to Zhang, incorporated herein by reference in it's entirety. For example, predetermined maximum and minimum intervals for the clean channel are identified from the updated buffer of 12 RR-intervals, Block 342 of FIG. 4. According to an embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated to generate an interval difference associated with the clean channel. A determination is then made as to whether the interval difference is greater than a predetermined stability threshold, such as 110 milliseconds, for example.

If the interval difference is greater than the stability threshold, the event is classified as an unstable event, and therefore the clean channel is determined not to include regular intervals, No in Block 348, and a determination is made as to whether the signal associated with the clean channel is within a predetermined VF shock zone, Block 350 of FIG. 4, described below. If the interval difference is less than or equal to the stability threshold, the device determines whether the minimum RR interval is greater than a minimum interval threshold, such as 200 milliseconds, for example.

If the minimum interval is less than or equal to the minimum interval threshold, the event is classified as an unstable event, and therefore the clean channel is determined not to include regular intervals, No in Block 348, and a determination is made as to whether the signal associated with the clean channel is within a predetermined VF shock zone, Block 350 of FIG. 4, described below. If the minimum interval is greater than the minimum interval threshold, the device determines whether the maximum interval is less than or equal to a maximum interval threshold, such as 333 milliseconds for example. If the maximum interval is greater than the maximum interval threshold, the event is classified as an unstable event and therefore the clean channel is determined not to include regular intervals, No in Block 348, and a determination is made as to whether the signal associated with the clean channel is within a predetermined VF shock zone, Block 350 of FIG. 4, described below. If the maximum interval is less than or equal to the maximum interval threshold, the event is classified as a stable event and therefore the clean channel is determined to include regular intervals, Yes in Block 348, and a determination is made as to whether the signal associated with the clean channel is within a predetermined VT shock zone, Block 352 of FIG. 4, described below.

The determination of whether the clean channel is within the VF shock zone, Block 350, is made based upon a low slope content metric and a spectral width metric, similar to the VF shock zone determination described above in reference to Blocks 360 and 362, both of which are determined for the clean channel using the method described above. Once the low slope content metric and a spectral width metric are determined for the clean channel, the determination of whether the clean channel is in the VF shock zone is made as described in U.S. Pat. No. 9,352,165 to Zhang, incorporated herein by reference in its entirety, so that if either the low slope content for the clean channel is not less than the first boundary or the spectral width is not less than the second boundary, the clean channel is determined not to be in the VF zone, No in Block 350 and both channels are classified as not shockable, Block 351, and the associated buffers are updated accordingly.

If the low slope content for the clean channel is less than the first boundary and the spectral width is less than the second boundary, the clean channel is determined to be in the VF zone, Yes in Block 350. A determination is then made as to whether the channel determined to be corrupted by noise, i.e., the "noisy channel", is within the VF shock zone, Block 354. If either the low slope content for the noisy channel is not less than the first boundary or the spectral width is not less than the second boundary, the noisy channel is determined not to be in the VF zone, No in Block 354, the clean channel is classified as shockable and the noisy channel is classified as not shockable, Block 355, and the associated buffers are updated accordingly.

If the low slope content for the noisy channel is less than the first boundary and the spectral width is less than the second boundary, the noisy channel is determined to be in the VF zone, Yes in Block 354, both the clean channel and the noisy channel are classified as being shockable, Block 353, and the associated buffers are updated accordingly.

Similar to the VT shock zone determination described above in reference to Block 358, during the determination as to whether the clean channel is within the VT shock zone in Block 352, the low slope content and the spectral width is determined for the clean channel as described above in reference to determining the VF shock zone. The first VT shock zone is defined based on the relationship between the low slope content and the spectral width associated with the clean channel and the second VT shock zone is defined based on the relationship between the low slope count and the normalized mean rectified amplitude associated with the clean channel. The normalized mean rectified amplitudes for the clean channel is the same as described above in reference to the noise detection tests of Block 344. For example, according to an embodiment of the present invention, the second VT shock zone is defined by a second boundary 526 associated with the relationship between the low slope count and the normalized mean rectified amplitude of the clean channel.

If both the low slope count is less than the first boundary and the normalized mean rectified amplitude is greater than the second boundary, the clean channel is determined to be in the VT shock zone, Yes in Block 352, both channels are classified as being shockable, Block 353, and the associated buffers are updated accordingly. If the clean channel is determined to be outside the VT shock zone, No in Block 352, both channels are classified as being not shockable, Block 351, and the associated buffers are updated accordingly.

According to an embodiment of the present disclosure, in addition to the classification of the sensing channels ECG1 and ECG2 as being shockable or not shockable using a gross morphology analysis, as described in FIG. 4, for example, the device also performs a beat-based analysis of the beats within each of the three-second windows, Block 368, so that the decision on state transitions (e.g. as to whether to transition from the concerned operating state 304 to the armed operating state 306 in Block 370, or from the armed state 306 to the shock state 308) is made based on the results of both an analysis of the gross morphology of the signal in the three-second window or windows for each sensing channel ECG1 and ECG2, and an analysis of the morphology of individual beats or R-waves in the three-second window or windows for each sensing channel ECG1 and ECG2, as described below. For a three-second segment to be classified as shockable, both the gross morphology and beat-based analysis have to classify the same three-second segment as shockable.

According to an embodiment, the device also determines a confidence level measurement during the beat-based analysis, Block 368, to determine whether the beat-based analysis may be corrupted by noise, and therefore determine whether the beat-based classification is verified. In this way, the device performs two separate noise determinations of the same signal within the same sensing channels ECG1 and ECG2 for use in the state transition decision, one determination during the gross morphology analysis, Block 342-346, and the second determination during the beat-based analysis, Block 368.

For example, according to an embodiment of the present invention, in order to determine whether to transition from the concerned operating state 304 to the armed operating state 306, the device determines whether a predetermined number, such as two out of three for example, of three-second segments for both channels ECG1 and ECG2 have been classified as being shockable during the gross morphology analysis, Blocks 353, 357, 363 and 369, and determines whether those three-second segments for both channels have also been classified as being shockable during the beat-based analysis, and/or whether the beat-based analysis for one or both of the channels may be corrupted by noise, Block 368. If the predetermined number of three-second segments in both channels ECG1 and ECG2 have been classified as shockable during both the gross morphology analysis and the beat-based analysis and noise determination, the device transitions from the concerned state 304 to the armed state 306, Yes in Block 370. When the device determines to transition from the concerned state 304 to the armed state 306, Yes in Block 370, processing continues to be triggered by a three-second time out as is utilized during the concerned state 304, described above.

If the predetermined number of three-second segments in both channels ECG1 and ECG2 have not been classified as shockable during both the gross morphology analysis and the beat-based analysis, the device does not transition from the concerned state 304 to the armed state 306, No in Block 370, and a determination as to whether to transition back to the not concerned state 302 is made, Block 372. The determination as to whether to transition from the concerned state 304 back to the not concerned state 302 is made, for example, by determining whether a heart rate estimate is less than a heart rate threshold level in both of the two channels ECG1 and ECG2, using the method for determining a heart rate estimate as described in U.S. Pat. No. 7,894,894 to Stadler et al., incorporated herein by reference in it's entirety. If it is determined that the device should not transition to the not concerned state 302, i.e., either of the two heart rate estimates are greater than the heart rate threshold, No in Block 372, the process continues using the signal generated during a next three-second window, Block 341.

As described above, the determination of whether the sensing channels ECG1 and ECG2 are shockable or not shockable, Blocks 353, 355, 357, and 363-369, is performed by analyzing the gross morphology of a sensed waveform occurring within the three-second windows. The ECG signal is segmented into n-second intervals, i.e., 3 second intervals that are used for determining gross morphology features of the three-second waveform. In particular, the gross morphology features are determined across an n-second time interval without relying on R-wave sensing and are therefore features making up the whole waveform signal that can be determined from the ECG signal independent of individual cardiac signals of the cardiac cycle, i.e., individual beats or R-waves contained within the three-second window that are within the entire three-second window. A single waveform in the n-second window begins at the start of the window, extends through entire window, ending at the end of the three-second window so that a single morphology determination is made for the single waveform included within the single three-second window.

On the other hand, multiple cardiac cycles, i.e, R-waves signals, are included within the three-second window, and therefore the n-second window may start and end at any time point relative to each of the individual R-wave signals irrespective of where an individual R-wave signal starts and ends, so that multiple individual beat-based determinations are made during the beat-based analysis for the multiple beat waveforms included within the single three-second window.

Morphology features computed for the single waveform extending across the n-second time period are referred to as "gross" morphology features because the features are characteristics of the single signal, extending from the start to the end of the window, that is extracted, independent of cardiac cycle timing, from a time segment that includes multiple individual cardiac cycles. In contrast, morphology features extracted from the ECG signal during a cardiac cycle are referred to as "beat-based" features. Beat-based features are determined from an ECG signal segment over a time interval of one cardiac cycle of multiple cardiac cycles contained within a single three-second window. Beat-based features may be averaged or determined from multiple cardiac cycles but are representative of a single feature of the ECG signal during a cardiac cycle. Determination of a beat feature is dependent on identifying the timing of a cardiac cycle, or at least a sensed event such as an R-wave, as opposed to determining gross features independent of the cardiac cycle over a time segment that is typically longer than one cardiac cycle.

Therefore, as described above, in addition to performing the morphology analysis of the whole waveform within the three-second windows associated with each sensing channel ECG1 and ECG2, the device performs a beat-based analysis of the signal sensed simultaneously within both channels ECG1 and ECG2, and/or whether the beat-based analysis for one or both of the channels is likely corrupted by noise Block 368. During the beat-based analysis, individual beats located within a three-second window are compared to a stored template, such as a normal sinus rhythm template, for example, to determine whether individual beats should be classified as a match beat or a non-match beat. The template may be input within the device manually by a clinician through visual analysis of ECG signals, or may be generated by the device after being implanted in the patient. For example, according to one embodiment, the device may generate the template using a fourth order signal of a predetermined number of beats, as described in commonly assigned U.S. patent application Ser. No. 13/826,097, incorporated herein by reference in it's entirety.

Figure 5:
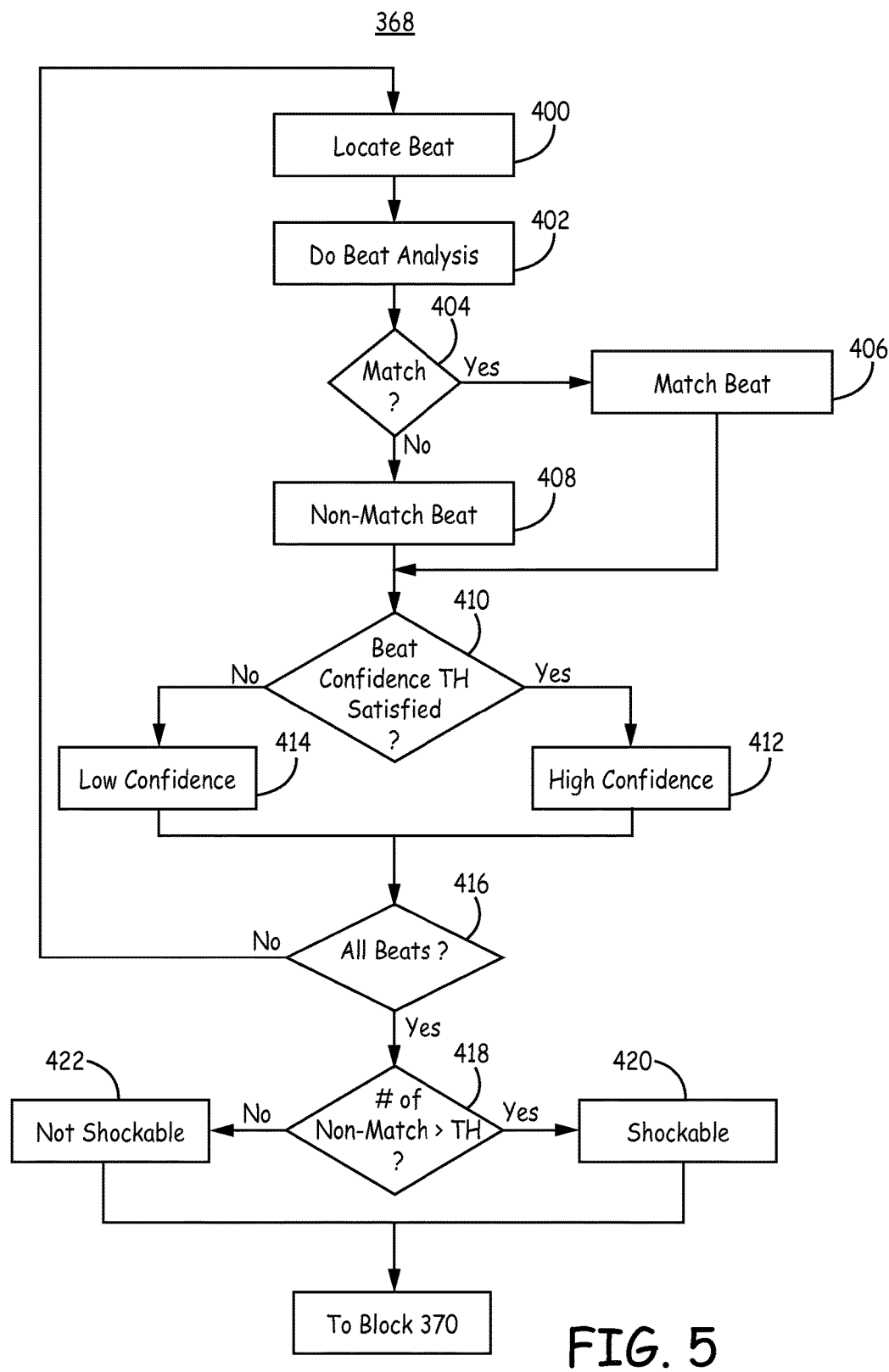
FIG. 5 is a flowchart of a method for performing beat-based analysis during detection of arrhythmias in a medical device, according to an embodiment of the present disclosure.

FIG. 5 is a flowchart of a method for performing beat-based analysis during detection of arrhythmias in a medical device, according to an embodiment of the present disclosure. Therefore, as described above, in addition to performing the morphology analysis of the whole waveform within the three-second windows associated with each sensing channel ECG1 and ECG2, the device performs a beat-based analysis of the signal sensed simultaneously within both channels ECG1 and ECG2, Block 368 of FIG. 4. In particular, as illustrated in FIG. 5, for each three-second sensing window associated with the respective sensing channels ECG1 and ECG2, the device locates a single beat, i.e., R-wave, of the multiple beats in the three-second window, Block 400, and performs a beat-based analysis of the single beat, Block 402. According to an embodiment, for example, during the beat-based analysis, Block 402, the device computes a normalized waveform area difference (NWAD) between the beat, also identified herein as "the unknown beat", and a predetermined beat template, such as a normal sinus rhythm template, for example, and determines whether the beat matches the template, Block 404, based on the determined normalized waveform area difference, as described below.

Using the results of the comparison of the beat to the template, the device determines whether the beat is either a match beat or a non-match beat, Block 404, by determining whether the beat matches the sinus rhythm template within a predetermined percentage, such as 60 percent, for example. If the beat matches the template by the predetermined percentage or greater, Yes in Block 404, the beat is identified as a match beat, Block 406. If the beat matches the template by less than the predetermined percentage, No in Block 404, the beat is identified as a non-match beat, Block 408.

Figure 6:
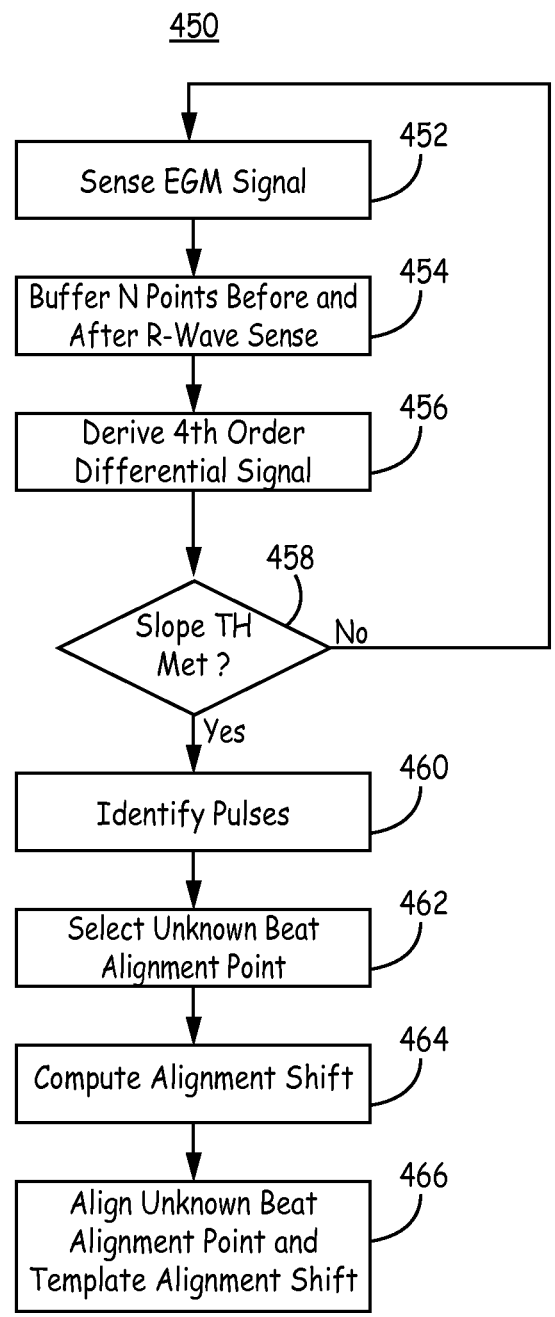
FIG. 6 is a flowchart of a method for aligning an ECG signal of an unknown beat with a known morphology template for beat-based analysis during detection of arrhythmias in a medical device, according to an embodiment of the present disclosure.

FIG. 6 is a flowchart of a method for aligning an ECG signal of an unknown beat with a known morphology template for beat-based analysis during detection of arrhythmias in a medical device, according to an embodiment of the present disclosure. In order to perform the comparison of the unknown beat with the template in Block 404 of FIG. 5 to identify the beat as being either a match beat or a non-match beat, the unknown beat must be aligned with the template. As illustrated in FIG. 6, during alignment of the unknown beat with the template, Block 450, the device identifies individual beats within the three-second window based on determined R-wave sense signals, Block 452, and for each beat stores n points before and n points after the sample point on which the R-wave sense occurs. The 2n+1 sample points define an alignment window within which an alignment point will be identified for alignment with the clinician input or device generated template, such as a normal sinus rhythm template, for example. In one embodiment, the alignment window is 53 sample points centered on the R-wave sense point. These sample points are stored in a memory buffer at block 454.

Once the sample points are determined for the beat, the device determines a fourth order difference signal for the beat from the buffered signal sample data, Block 456. The maximum slope of the fourth order difference signal is determined and compared to a maximum slope threshold, e.g. approximately 136 analog-to-digital (A/D) conversion units, Block 458. If the slope threshold is not met, No in Block 458, the signal may be rejected as a weak signal, no further analysis of that beat is performed, and the process continues with the next beat in the three-second window, Block 452. If the maximum slope is greater than the threshold, Yes in Block 458, indicating that at least one pulse corresponding to an R-wave is likely to be present in the alignment window, pulses associate with the individual beat within the alignment window are identified, Block 460.

To identify pulses associated with the beat within the alignment window, pulse criteria may be established, such as having a pulse width equal to at least some minimum number of sample points and a pulse amplitude of at least some minimum amplitude. The number of pulses identified, or lack thereof, within the alignment window may be used to reject a "cardiac cycle" as a noisy cycle or a weak signal. One or more pulses, including negative-going and positive-going pulses, may be identified according to amplitude and pulse width criteria. In some examples, a pulse may be identified based on a slope, maximum peak amplitude (positive or negative), pulse width or any combination thereof. If a threshold number of pulses is identified within the alignment window, the cycle may be considered a noisy cycle. While not shown explicitly in FIG. 6, a noisy cycle may be flagged or rejected for use in morphology analysis.

After identifying all pulses from the fourth order difference signal in the alignment window, a pulse having a maximum pulse amplitude and having the same polarity as a stored template alignment point is identified, Block 462. The sample point having the maximum pulse amplitude (absolute value) that also matches the polarity of the template alignment point is identified and defined as the unknown signal alignment point.

An alignment shift is computed, Block 464, as the difference in sample point number between the alignment point identified, Block 462, and the previously established template alignment point. The alignment shift is the number of sample points that the unknown beat must be shifted in order to align the unknown signal alignment point with the template alignment point. The alignment shift is applied by shifting the unknown beat sample points to align the unknown beat and the template over the alignment window, Block 466. The alignment shift may be applied to the fourth order difference signal itself if the template is stored as an ensemble average of aligned fourth order difference signals or stored as the fourth order difference signal of an ensemble average of aligned raw ECG signals. The alignment shift may additionally or alternatively be applied to the digitized raw signal sample points of the unknown signal when the template is the ensemble average of the raw signal sample points acquired during a known rhythm and aligned using the fourth order difference signal, as described in the template generation described in commonly assigned U.S. patent application Ser. No. 13/826,097, incorporated herein by reference in it's entirety. In another variation, the template may be the fourth order difference signal of ensemble averaged raw signals, and the fourth order difference signal of the unknown raw signal is aligned with the fourth order difference template.

Figure 7:
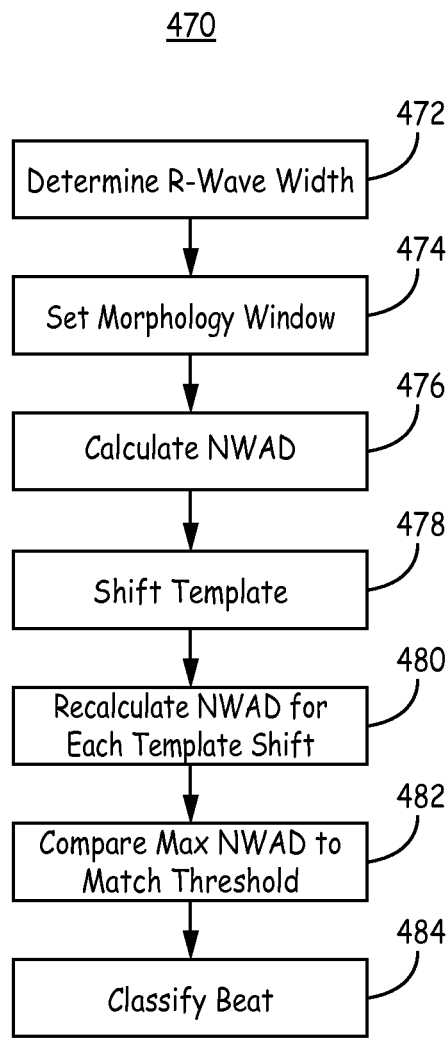
FIG. 7 is a flowchart of a method for computing a morphology metric to determine the similarity between a known template aligned with an unknown cardiac cycle signal according to one embodiment.

FIG. 7 is a flowchart of a method for computing a morphology metric to determine the similarity between a known template aligned with an unknown cardiac cycle signal according to one embodiment. After aligning the unknown beat and the template using the fourth order difference signal alignment points, the morphology between the unknown beat and the template is compared, Block 470. Numerous types of morphology analysis could be used, such as wavelet analysis, comparisons of fiducial points (peak amplitude, zero crossings, maximum slopes, etc.) or other techniques. In one embodiment, a NWAD is computed using a morphology analysis window that is a subset of, i.e. a number of sample points less than, the alignment window.

The operations performed by the device as described in conjunction with FIG. 7 may be performed on the aligned raw signal and corresponding template and/or the aligned fourth order difference signal and corresponding fourth order difference signal template.

As illustrated in FIG. 7, during the comparing of an individual beat with the beat template, the device determines the R-wave width of the unknown signal, Block 472. In an illustrative embodiment, in order to determine the R-wave width, the device determines an onset and an offset point of the R-wave. During the determination of the onset and offset, the maximum positive pulse and the maximum negative of the fourth order difference signal are identified. The maximum positive pulse is an identified pulse having positive polarity and maximum positive peak value; the maximum negative pulse is an identified pulse having negative polarity and maximum absolute peak value. If the R wave has a positive polarity in the raw ECG signal, the maximum positive pulse will precede the maximum negative pulse on the $4^{th}$-order difference waveform. An onset threshold is set based on the amplitude of the maximum positive pulse and an offset threshold is set based on the amplitude of the maximum negative pulse. For example, one-eighth of the peak amplitude of the maximum positive pulse may be defined as the onset threshold and one eighth of the negative peak amplitude of the maximum negative pulse may be defined as the offset threshold.

The onset of the R-wave is identified as the first sample point to the left of the maximum positive pulse (e.g. moving from the pulse peak backward in time to preceding sample points) to cross the onset threshold. The offset of the R-wave is identified as the first sample point to the right of the maximum negative pulse crossing the offset threshold. The R-wave width is the difference between the onset sample point number and the offset sample point number, i.e. the number of sampling intervals between onset and offset.

For an R-wave having a negative polarity on the raw waveform, the maximum negative pulse will precede the maximum positive pulse on the fourth order difference signal. As such, the onset threshold is set as a proportion of the maximum negative peak amplitude of the maximum negative pulse of the fourth order difference signal, and the offset threshold is set as a proportion of the maximum positive peak amplitude of the maximum positive pulse. The R-wave onset is detected as the first sample point to cross the onset threshold when moving left (earlier in time) from the maximum negative peak. The R-wave offset is detected as the first sample point to cross the offset threshold moving right (later in time) from the maximum positive peak. The R-wave width is the difference between the onset sample point and the offset sample point. This method of computing an R-wave width based on onset and offset points identified from the fourth order difference signal is illustrated below in FIG. 9.

The device sets a morphology analysis window in response to the R-wave width determined from the fourth order difference signal, Block 474. The morphology of the R-wave itself is of greatest interest in classifying the unknown beat. Processing time can be reduced by comparing only the sample points of greatest interest without comparing extra points, for example baseline points or Q- or S-wave points, preceding or following the R-wave. The morphology analysis window is therefore a proportion of the sample points that is less than the total number of sample points aligned in the alignment window.

In one embodiment, different ranges of R-wave width measurements may be defined for which different respective sample numbers will be used to set the morphology analysis window. For example, if the R-wave width is greater than 30 sample intervals, the morphology analysis window is set to a first number of sample points. If the R-wave width is greater than 20 sample intervals but less than or equal to 30 sample intervals, the morphology analysis window is set to a second number of sample points less than the first number of sample points. If the R-wave width is less than or equal to 20 sample points, the morphology analysis window is set to a third number of sample points less than the second number of sample points. Two or more R-wave width ranges may be defined, each with a corresponding number of sample points defining the morphology analysis window. At least one of the R-wave width ranges is assigned a number of sample points defining the morphology analysis window to be less than the alignment window. In some embodiments all of the R-wave width ranges are assigned a number of sample points defining the morphology analysis window to be less than the alignment window.

In the example given above, the alignment window is 53 sample points. If the R-wave width is greater than 30 sample intervals, the morphology window is defined to be 48 sample points. The morphology analysis window may include 23 points preceding the R-wave sense point, the R-wave sense point itself, and 24 points after the R-wave sense point. If the R-wave width is greater than 20 but less than or equal to 30 sample intervals, the morphology window is defined to be 40 sample points (e.g. 19 before the R-wave sense point and 20 after the R-wave sense signal). If the R-wave width is less than or equal to 20 sample intervals, the window is defined to be 30 sample points (e.g. 14 before and 15 points after the R-wave sense point and including the R-wave sense point).

In other embodiments, the number of sample points in the morphology analysis window may be defined as a fixed number of sample points greater than the R-wave width, for example the R-wave width plus 12 sample points. In another example, the number of sample points defining the morphology analysis window may be computed as the R-wave width plus a rounded or truncated percentage of the R-wave width. For example, the morphology analysis window may be defined as the R-wave width plus fifty percent of the R-wave width (i.e. 150% of the R-wave width), up to a maximum of the total alignment window or some portion less than the total alignment window.

The morphology window is applied to both the unknown beat and the template. With the template and unknown cardiac signal aligned within the alignment window, the same number of sample points taken prior to and after the unknown beat alignment point is taken prior to and after the template alignment point.

After setting the morphology analysis window, Block 474, a morphology metric of the similarity between the unknown signal and the template, such as the normalized waveform area difference (NWAD), for example, is computed, Block 476. Different methods maybe used to compute a NWAD. In an illustrative method, the NWAD is computed by normalizing the absolute amplitude of each of the unknown beat sample points and the template sample points within the morphology window by a respective absolute maximum peak amplitude value. A waveform area difference is then calculated by summing the absolute amplitude differences between each aligned pair of normalized sample points in the unknown signal and in the template over the morphology window.

This waveform area difference may be normalized by a template area. The template area is computed as the sum of all of the absolute values of the normalized template sample points in the morphology window. The NWAD is then calculated as the ratio of the waveform area difference to the template area. The NWAD for the aligned signals is stored.

This NWAD may be compared to a threshold to classify the unknown beat as matching the template based on a high correlation between the unknown beat and the template evidenced by a NWAD exceeding a match threshold. One or more NWADs may be computed for a given unknown beat. In the example shown in FIG. 7, additional NWADs may be computed by shifting the aligned template relative to the already aligned unknown signal by one or more sample points, Block 478. In one embodiment, the template is shifted by one sample point to the right, two sample points to the right, one sample point to the left and two sample points to the left to obtain five different alignments of the template and unknown signal. For each template alignment, i.e. with alignment points aligned, and with template and unknown signal alignment points shifted relative to each other by one point and two points in each direction, a NWAD is computed, Block 480. In this way, five NWADs are computed to measure the similarity between the unknown beat and the template (in aligned and shifted positions).

The device selects the NWAD having the greatest value as the morphology metric for the unknown beat, which is then compared to the match threshold, Block 482, to classify the unknown beat as being either a match beat or a non-match, Block 484, as described above in Blocks 404-408 of FIG. 5.

Figure 8:
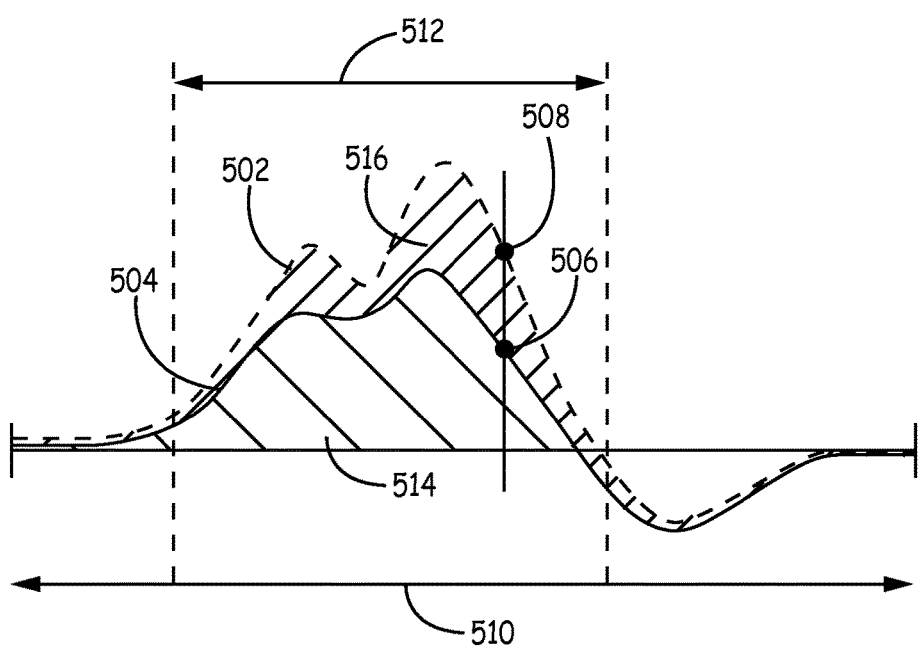
FIG. 8 is an exemplary plot of alignment of an unknown beat and a template for computing a normalized waveform area difference during beat-based analysis, according to one embodiment.

FIG. 8 is an exemplary plot of alignment of an unknown beat and a template for computing a normalized waveform area difference during beat-based analysis, according to one embodiment. As illustrated in FIG. 8, the unknown raw ECG signal 502 and the raw ECG signal template 504 (ensemble average of n raw signals aligned using fourth order difference signal) are used for determining a morphology match metric over a morphology analysis window 512. The width of the morphology analysis window 512 and the alignment of the unknown signal 502 and template 504 are based on analysis of fourth order difference.

The raw ECG signal 502 is aligned with a template alignment point 506 of the template 504 of the raw ECG signal established during NSR, identified from an ensemble averaged fourth order difference signal as the maximum absolute pulse amplitude value. An unknown signal alignment point 508 is identified from the fourth order difference signal of the unknown raw ECG signal 502. The unknown signal alignment point 508 is the maximum absolute pulse amplitude value having the same polarity as the template alignment point 506.

After aligning the template 504 with the unknown raw ECG signal 502 over an alignment window 510, a morphology window 512 is set. The morphology window 512 is a subset of, i.e. shorter than or fewer sample points than, the alignment window 510. The morphology window 512 is set based on an R-wave width measured from the fourth order difference signal of the unknown signal as described below in conjunction with FIG. 9. The morphology analysis window 512 is set in response to the R-wave width measurement as some sample number greater than the R-wave width, as described above.

The device determines a template area 514 as the sum of all of the normalized absolute values of the template sample points within the morphology analysis window 512. The values are normalized by the absolute value of the maximum amplitude of the template. The waveform area difference 516 is computed as the summation of the absolute values of the differences between the aligned normalized absolute values of the unknown ECG signal sample points and the normalized absolute values of the template sample points. The NWAD is determined by taking the ratio of the waveform area difference 516 to the template area 514, which is then used in the determination, Block 404, of whether the unknown beat is a match beat, Block 406, or a non-match beat, Block 408, in FIG. 5.

Figure 9:
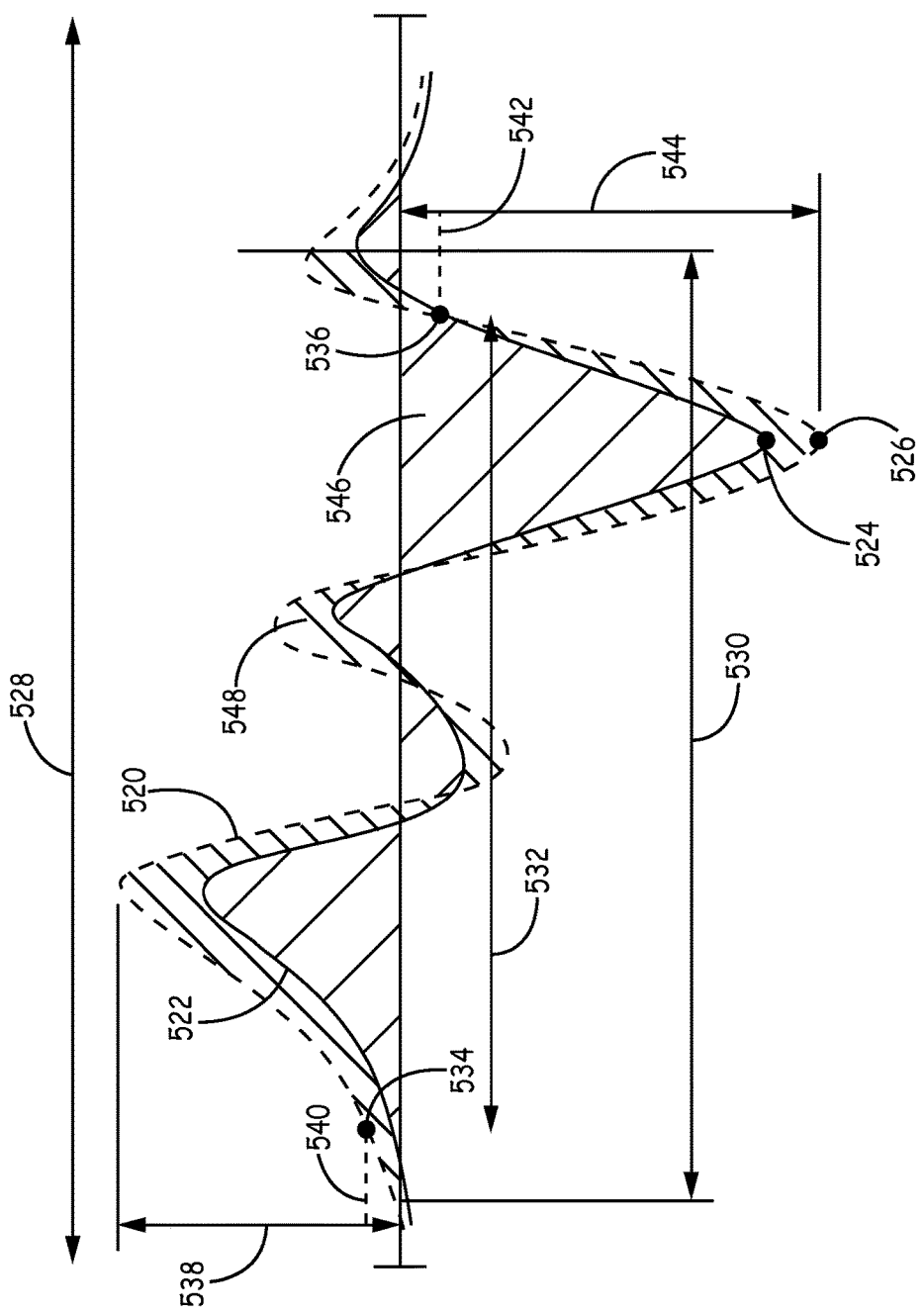
FIG. 9 is an exemplary plot illustrating a technique for determining an R-wave width and computing a normalized waveform area difference during beat-based analysis, according to another embodiment.

FIG. 9 is an exemplary plot illustrating a technique for determining an R-wave width and computing a normalized waveform area difference during beat-based analysis, according to another embodiment. In the example illustrated in FIG. 9, a fourth order difference signal 520 of the unknown raw ECG signal is aligned with a fourth order difference signal template 522 for determining a morphology match metric over a morphology analysis window 530.

The unknown fourth order difference signal 520 is derived from the unknown raw ECG signal sensed by the device and is aligned with the fourth order difference template 522 established during NSR. The template alignment point 524 is identified as the maximum absolute pulse amplitude value of the fourth order difference template. The unknown signal alignment point 526 is identified as the maximum absolute pulse amplitude value having the same polarity as the template alignment point 524. The unknown fourth order difference signal 520 is shifted over the alignment window 528 by an alignment shift required to align the unknown signal alignment point 526 with the template alignment point 524 as shown.

After aligning the template 522 with the unknown fourth order difference signal 520 over alignment window 528, a morphology window 530 is set. The morphology window 530 is a subset of the alignment window 528 and is based on an R-wave width 532 measured from the unknown fourth order difference signal 520.

In order to determine the R-wave width 532, the device determines the difference between an R-wave onset point 534 and an R-wave offset point 536 of the fourth order difference signal 520 of the unknown beat. In order to determine an R-wave onset point 534, the device determines a maximum positive pulse peak amplitude 538, and sets an onset threshold 540 as a proportion of the maximum positive pulse peak amplitude 538. In one embodiment, the device sets the onset threshold 540 as one-eighth of the maximum positive pulse peak amplitude 538. The onset point 534 is identified as the first point to the left of the maximum positive pulse peak crossing the onset threshold 540, i.e. equal to or greater than the onset threshold 540.

The device sets an offset threshold 542 as a proportion of a maximum negative pulse peak amplitude 544, and the offset point 536 is identified as the first point crossing the offset threshold 542 to the right of the maximum negative pulse. The device determines the R-wave width 532 as being the difference between the onset point 534 and the offset point 536. The morphology analysis window 530 is set in response to the R-wave width measurement as some sample number greater than the R-wave width 532, as described previously.

In other examples, the maximum negative pulse may occur earlier in the alignment window than the maximum positive pulse. If this is the case, the onset threshold is set as a proportion of the maximum negative pulse peak amplitude and the onset point is determined as the first point crossing the onset threshold to the left of the maximum negative peak. Likewise, the offset threshold is set as a proportion of the maximum positive pulse peak amplitude, and the offset point is determined as the first point to the right of the maximum positive pulse to cross the offset threshold.

The morphology analysis window 530 may be centered on an R-wave sense signal. In some embodiments, the morphology analysis window 530, determined from the fourth order difference signal 520, is applied to the unknown raw ECG signal aligned with a raw ECG signal template, for example analysis window 512 as shown in FIG. 8. The morphology match metric is determined from the raw ECG signal 502 and template 504. In the example illustrated in FIG. 9, the morphology analysis window 530 is applied to the fourth order difference signal 520; the morphology match metric is determined from the fourth order difference signal 520 and fourth order difference template 522.

The template area 546 is computed as the sum of all of the normalized absolute values of the template sample points within the morphology window 530. The values are normalized by the absolute value of the maximum amplitude of the template 522 (in this example point 526). The device determines the waveform area difference 548 as the summation of the absolute differences between the aligned normalized absolute values of the unknown fourth order difference signal sample points and the normalized absolute values of the template sample points. The NWAD is determined by the device as the ratio of the waveform area difference 548 and the template area 546, and is compared to a match threshold to classify the unknown beat corresponding to the fourth order difference signal 520 as being either a match beat or a non-match beat, Blocks 406 and 408 of FIG. 5.

Returning to FIG. 5, once the individual beat is identified as being either a match beat, Block 406, or a non-match beat, Block 408, using the normalized waveform area difference analysis described above, the device determines whether the individual beat may be corrupted, such as by noise, for example, thereby reducing the level of confidence in the determination that the beat is either a match beat, Block 406, or a non-match beat, Block 408. Based on the determined level of confidence, the device may determine that the beat should be discarded in the beat-based shockable/not shockable analysis for the three-second window, as described below.

If the beat confidence threshold is satisfied, Yes in Block 410, the beat is considered a high confidence beat and therefore is identified as a beat that should not be discarded, Block 412. If the beat confidence threshold is not satisfied, No in Block 410, the beat is considered a low confidence beat and therefore is identified as a beat that should be discarded, Block 414. Once the beat is identified as either being a high confidence beat, Block 412, or a low confidence beat, Block 414, the device determines whether the determination has been made for all of the beats in the three-second window, Block 416. If the determination has not been made for all of the beats in the three-second window, the process of identifying a beat as being either a match beat or a non-match beat and a high confidence beat or a low confidence beat, Blocks 400-414, is repeated for the next beat.

Figure 10:
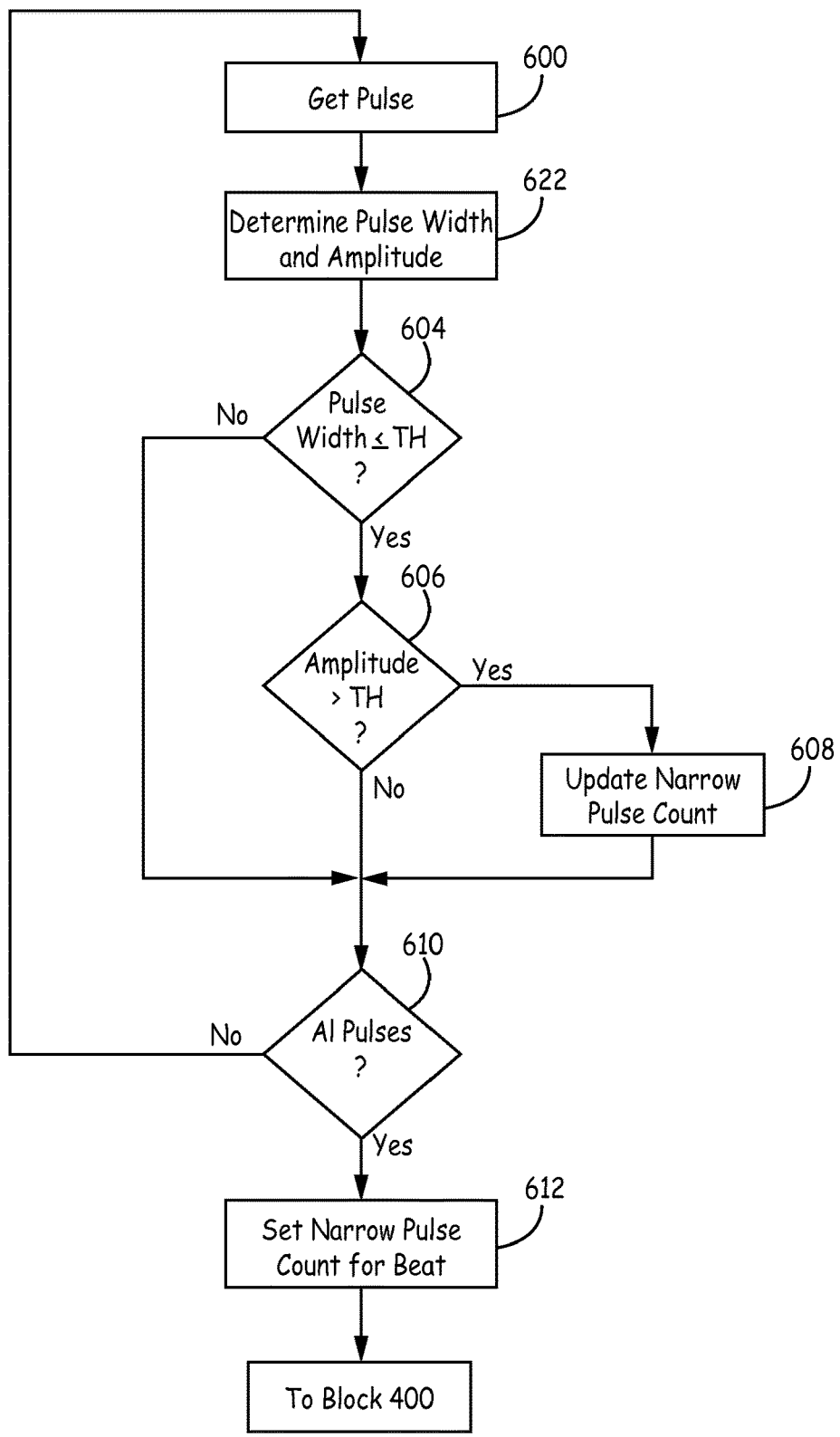
FIG. 10 is a flowchart of a method for determining an individual beat confidence during beat-based analysis, according to one embodiment.

FIG. 10 is a flowchart of a method for determining an individual beat confidence during beat-based analysis, according to one embodiment. In order to determine whether the beat confidence threshold is satisfied in Block 410 of FIG. 5, the device determines a narrow pulse count, i.e., pulse number, for the plurality of pulses associated with the beat using parameters previously determined during the normalized waveform area difference analysis in Block 402, described above.

For example, in order to determine the narrow pulse count for each individual beat, the device determines, for each individual pulse of the pulses identified in the alignment window for the beat during the alignment of the unknown beat with the template, Block 460 of FIG. 6, whether the width of the pulse is less than a predetermined threshold. In particular, as illustrated in FIG. 10, the device gets a single pulse of the identified pulses for the beat, Block 600, determines a pulse width associated with the pulse, Block 6022, and determines whether the pulse width is less than or equal to a pulse width threshold, Block 604.

In addition to determining whether the pulse width of the individual pulse is less than or equal to the pulse width threshold, Yes in Block 604, the device also determines whether the absolute amplitude of the pulse is greater than an amplitude threshold, Block 606. According to an embodiment, the pulse width threshold may be set as 23 milliseconds, for example, and the amplitude threshold is set as a fraction, such as one eighth, for example, of the maximum slope used in the determination of whether the slope threshold was met during the aligning of the beat with the template, Block 458 of FIG. 6.

While the pulse width determination, Block 604, is illustrated as occurring prior to the amplitude threshold determination, Block 606, it is understood that the sequence of the determinations of Blocks 604 and 606 is not overriding. Therefore, if either the pulse width of the individual pulse is not less than or equal to the pulse width threshold, No in Block 604, or the absolute amplitude of the pulse is not greater than the amplitude threshold, No in Block 606, the pulse is determined not to be included in the narrow pulse count. The device continues by determining whether the determination of whether the number of pulses satisfying the narrow pulse count parameters has been made for all of the identified pulses (Block 460 of FIG. 6) for the beat, Block 610. If the determination has not been made for all of the identified pulses, No in Block 610, the device identifies the next pulse, Block 600, and the process of determining a narrow pulse count for that beat, Blocks 602-608, is repeated for the next pulse.

If both the pulse width of the individual pulse is less than or equal to the pulse width threshold, Yes in Block 604, and the absolute amplitude of the pulse is greater than the amplitude threshold, Yes in Block 606, the number of pulses satisfying the width and amplitude thresholds for the individual beat, i.e., the narrow pulse count, is increased by one, Block 608.

Once the determination has been made for all of the identified pulses associated with the beat, Yes in Block 610, the device sets the narrow pulse count for the beat, Block 612, equal to the resulting updated narrow pulse count, Block 608. In this way, the narrow pulse count for the beat is the total number of pulses of the identified pulses for the beat that satisfy both the width threshold, i.e., the number of pulses that have a pulse width less than 23 milliseconds, and the amplitude threshold, i.e., the number of pulses that have an absolute amplitude greater than one eighth of the maximum slope used in the determination of whether the slope threshold was met during the aligning of the beat with the template, Block 456 of FIG. 6. The final narrow pulse count from Block 612 is then used by the device in the determination of whether the beat confidence threshold is satisfied for the beat, Block 410 of FIG. 5.

Returning to FIG. 5, when determining whether the beat confidence threshold has been satisfied for the beat, the device determines compares the narrow pulse count for the beat obtained from Block 612 of FIG. 10 to a narrow pulse count threshold, such as 5, for example. If the narrow pulse count is less than the narrow pulse count threshold, the beat confidence threshold is satisfied, Yes in Block 410, the beat is considered a high confidence beat and therefore is identified as a beat that should not be discarded, Block 412. If the narrow pulse count is not less than the narrow pulse count threshold, the beat confidence threshold is not satisfied, No in Block 410, the beat is considered a low confidence beat and therefore is identified as a beat that should be discarded, Block 414.

Once the determination of the beat being either a match beat or a non-match beat, and either a high confidence or a low confidence beat has been made for all of the beats in the three-second window, Yes in Block 416, a determination is made as to whether the number of non-match beats in the three-second window that are also high confidence beats is greater than a non-match threshold, Block 418. According to an embodiment of the disclosure, the non-match threshold is set as a predetermined percentage, such as 75 percent for example, so that if the number of individual beats in the three-second window that are identified as being non-match beats is greater than 75 percent of the number of all of the beats in the window, Yes in Block 418, the three-second window is identified as being shockable based on the beat-based analysis, Block 420.

On the other hand, if the number of individual beats in the three-second window that are identified as being both non-match beats and high confidence beats is not greater than 75 percent of the number of all of the beats in the window, No in Block 418, the three-second window is identified as being not shockable based on the beat based analysis, Block 422. The beat-based analysis determination of the three-second windows as being shockable 420 or not shockable, Block 422 is then used in combination with the waveform morphology analysis of both of the three-second windows being shockable, Blocks 353, 357, 363 and 369 or both not shockable, Blocks 351, 355, 359, 365 and 367 to determine whether to transition to the next state, Block 370, as described above.

Figure 11:
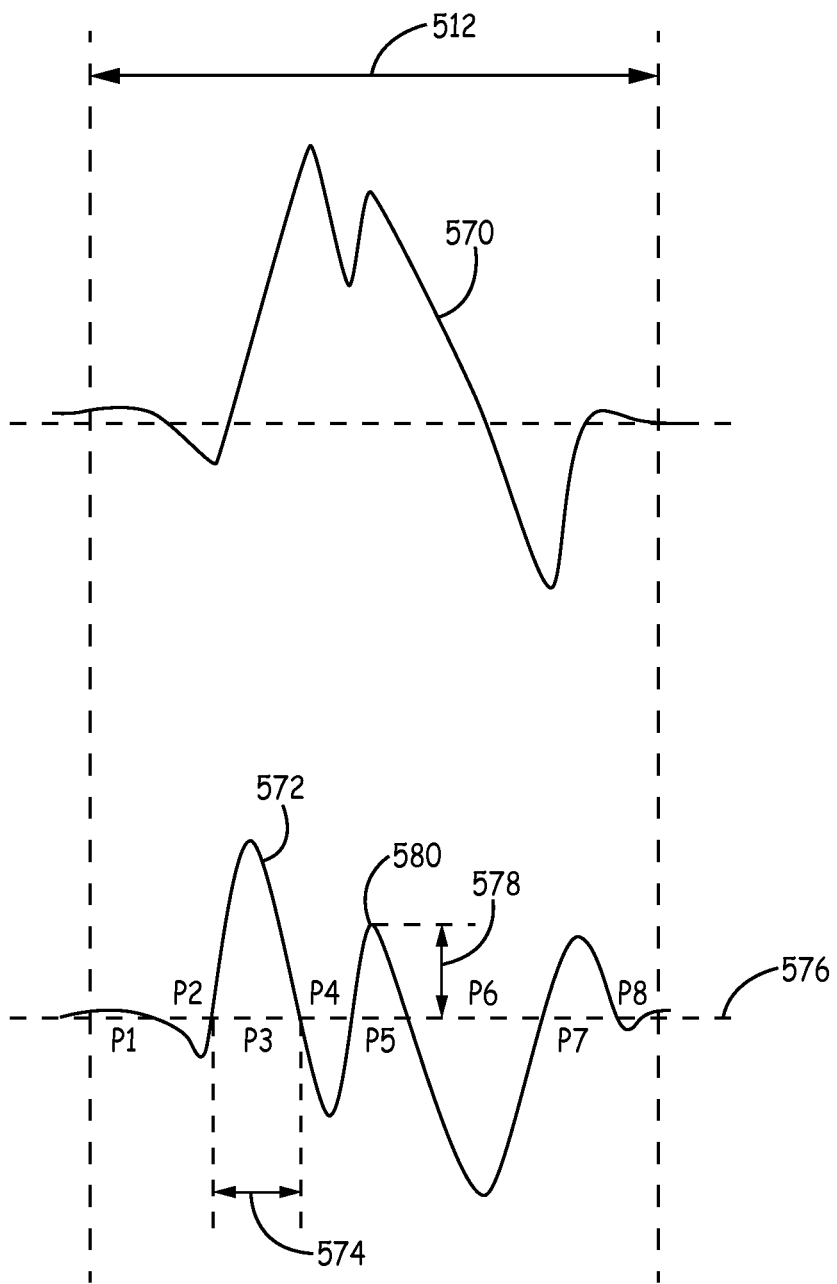
FIG. 11 is an exemplary plot illustrating determining pulses for a beat within a window during a beat-based analysis according to an embodiment of the disclosure.

FIG. 11 is an exemplary plot illustrating determining pulses for a beat within a window during a beat-based analysis according to an embodiment of the disclosure. As illustrated in FIG. 11, the device senses each individual R-wave 570 occurring within a three-second window, determines a morphology window 512, and determines a number of pulses, i.e., pulse count, associated with the R-wave 570 from the fourth order difference of the R-wave 572 within the morphology window 512 for use in determining a beat confidence for the R-wave 570, as described above. For example, in response to the fourth order difference 572 of the sensed R-wave 570, the device determines there are eight pulses P1-P8 associated with the R-wave 570. Pulses P1, P3, P5 and P7 are positive pulses and P2, P4, P6 and P8 are negative pulses, with each pulse P1-P8 having a pulse width 574 defined by zero-crossings of the pulses with a baseline 576, and a pulse amplitude 578 defined between a pulse peak 580 and the baseline 576. In this way, the device uses the determined pulses P1-P8 and their associated pulse width 574 and pulse amplitude 578 to determine a narrow pulse count, as described above.

Figure 12:
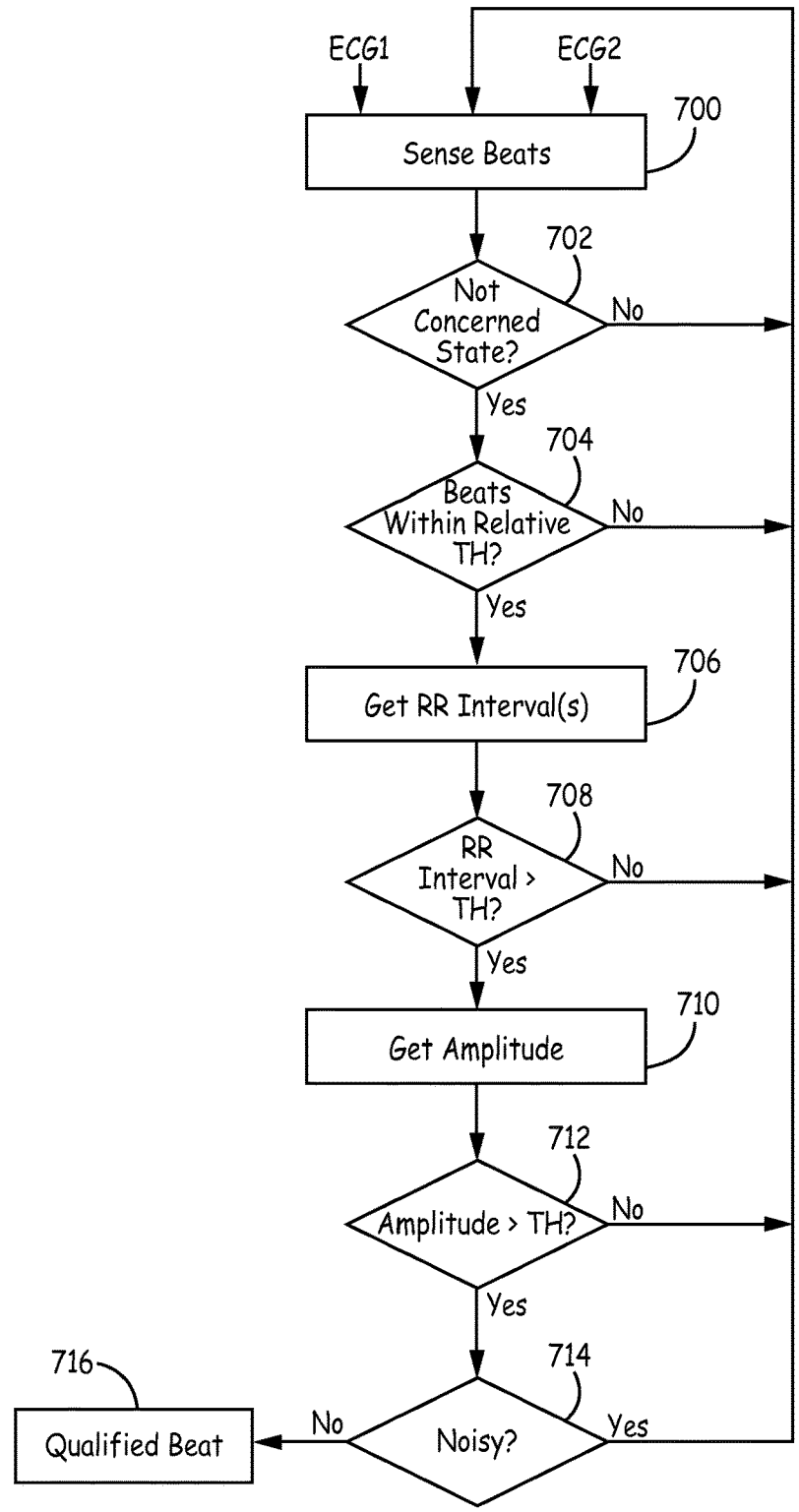
FIG. 12 is a flowchart of a method for acquiring beats for generating a template according to an embodiment of the disclosure.

FIG. 12 is a flowchart of a method for acquiring beats for generating a template according to an embodiment of the disclosure. As illustrated in FIG. 12, in order to determine desirable beats to be utilized during template generation, the device identifies beats during sensing of the cardiac signal along each sensing vector ECG1 and ECG2, Block 700, and determines whether the device is in the not concerned operating state 302, Block 702. If the device is not in the not concerned operating state, No in Block 702, the corresponding sensed beat is ignored as a candidate beat for generating a template, and the process is repeated with the next beat, Block 700. If the device is in the not concerned operating state, Yes in Block 702, the device determines whether the beats for each sensing vector ECG1 and ECG2 are within a predetermined relative threshold, Block 704.

For example, according to one embodiment, in order to determine whether a beat sensed for one sensing vector ECG1 is within a relative threshold of a beat simultaneously sensed in the other sensing vector ECG2, the device compares the sensing marker associated with the sensing of the beat sensed for one sensing vector ECG1 with the beat sensed for the other sensing vector ECG2. If the difference between the values of the two sensing markers are within a predetermined range, such as within 60 ms or less of each other, for example, the beats are determined to be within the relative threshold, Yes in Block 704. If the difference between the values of the two sensing markers are not within the predetermined range, i.e., the difference is greater than 60 ms, the beats are determined not to be within the relative threshold, No in Block 704, and the current beats are discarded and the process is repeated with the next beat, Block 700.

In this way, comparing the difference between sensing marker values for simultaneously sensed beats sensed by the two sensing vectors, the device addresses possible instances of oversensing by avoiding oversensed beats that may occur due to P-wave, T-wave, wide QRS, or noise/artifacts within one of the sensing vectors but not the other sensing vector. If the simultaneously sensed beats form the two sensing vectors are determined to be within the relative threshold, Yes in Block 704, the device determines whether RR-intervals forming the current beat simultaneously sensed for each sensing vector, Block 706, are within a predetermined interval threshold, Block 708. The interval threshold is chosen so as to insure that the beats used to generate the template are acquired during instances of the patient having a slow heart rate, such as less than 100 beats per minute, for example.

Figure 12A:
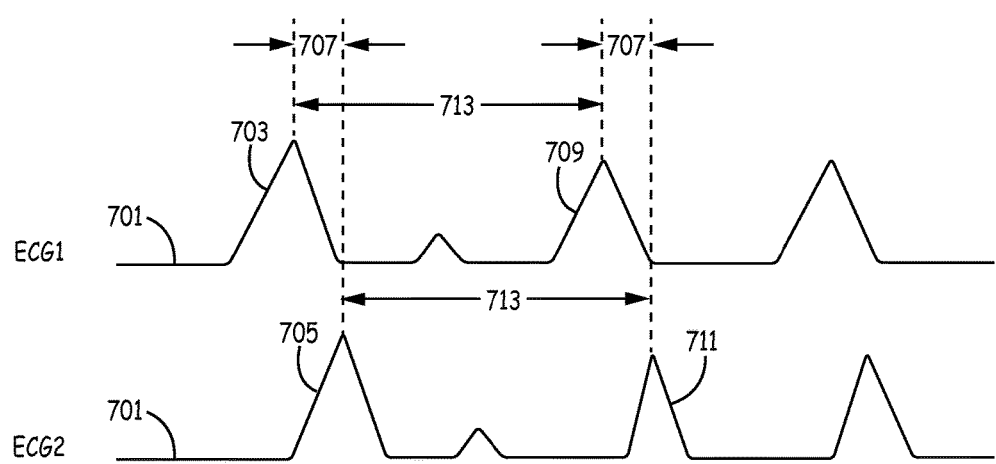
FIG. 12A is a schematic diagram of detection of simultaneously sensed R-waves sensed along two sensing vectors according to an embodiment of the disclosure.

FIG. 12A is a schematic diagram of detection of simultaneously sensed R-waves sensed along two sensing vectors according to an embodiment of the disclosure. As illustrated in FIGS. 12 and 12A, a cardiac signal 701 is sensed along both of the two sensing vectors ECG1 and ECG2, and the device determines that a sensed R-wave 709 sensed along one sensing vector ECG1 and a sensed R-wave 711 sensed along the other sensing vector ECG2 are simultaneously sensed when a difference 707 between the R-waves 709 and 711 is less than the relative threshold, as described above. In order to determine an RR-interval associated with currently sensed simultaneously sensed RR intervals, Block 700, the device determines previous simultaneously sensed R-waves in the two sensing vectors, R-wave 703 and 705, and determines, separately for each sensing vector ECG1 and ECG2, whether a resulting interval 713 associated with the simultaneously sensed R-waves 703, 705, 709 and 711 is less than the interval threshold, block 708.

If the RR-interval 713 forming the current simultaneously sensed beats 703, 705, 709 and 711 for each sensing vector, Block 706, is not within the predetermined interval threshold, No in Block 708, i.e., not less than 100 beats per minute, the current beats are discarded and the process is repeated with the next beat, Block 700. On the other hand, if the RR-interval forming the current simultaneously sensed beats 705, 707, 709 and 711 is within the predetermined interval threshold, Yes in Block 708, the device determines, for each sensing vector ECG1 and ECG2 whether the maximum absolute pulse amplitude value 524 determined as described above for both the beat from the first sensing vector ECG1 and the beat from the second sensing vector ECG2, Block 710, are greater than a maximum amplitude threshold, Block 712, such as 50 µV, for example.

If the maximum amplitudes for both sensing vectors are not determined to be greater than the amplitude threshold, No in Block 712, the current beats are discarded and the process is repeated with the next beat, Block 700. If the maximum amplitude for only one sensing vector is determined to be greater than the amplitude threshold, Yes in Block 712, the sensing channel not satisfying the amplitude threshold is discarded, and the device determines whether the sensing channel satisfying the amplitude threshold is a clean channel, i.e., not noisy, Block 714, and if the sensing channel satisfying the amplitude threshold is a clean channel, No in Block 714, the beat for that channel is determined to be a qualified beat, Block 716, for generating a template, as described below. If the sensing channel satisfying the amplitude threshold is not a clean channel, the beat for that channel is also discarded and the process is repeated with the next beats, Block 700. For example, in order to determine whether the individual sensing channel ECG1 and ECG2 is noisy in Block 714, the device determines whether the number of narrow pulses determined in a narrow pulse count described above for that sensing channel or channels, is less than a pulse count threshold, such as 6 pulses for example.

If the maximum amplitudes for both sensing vectors are determined to be greater than the amplitude threshold, Yes in Block 712, the device determines whether both sensing channels are clean channels, Block 714, and if one channel is clean and the other channel is not, the beat associated with the clean channel is identified as a qualified beat, Block 716, and the other beat is discarded and the process is repeated with the next beats. If the maximum amplitudes for both sensing vectors are determined to be greater than the amplitude threshold, Yes in Block 712, and both are determined to be clean, No in Block 714, both beats are identified as being qualified beats, Block 716, for generating a template, as described below.

If both sensing channels are determined to satisfy the amplitude threshold, Yes in block 712, but both are determined not to be clean channels, Yes in Block 714, the current beats are discarded and the process is repeated with the next beat, Block 700. In this way, the determination of whether the amplitude of the beats in the two channels are greater than the amplitude threshold, Block 712 and the determination of whether the channels are clean, Block 714, is performed individually for both sensing vectors.

Figure 13:
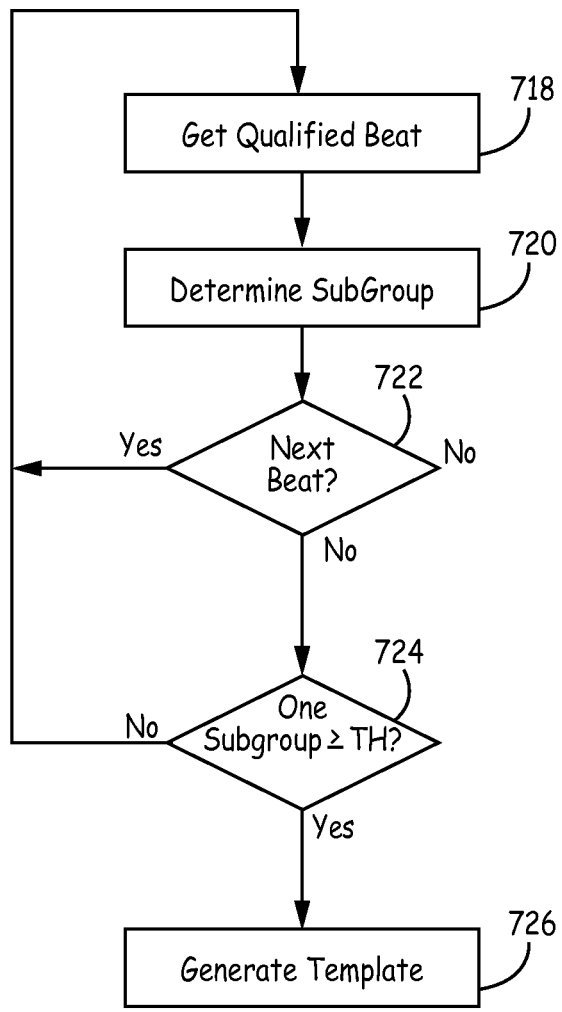
FIG. 13 is a flowchart of generating a template according to an embodiment of the disclosure.

FIG. 13 is a flowchart of generating a template according to an embodiment of the disclosure. Using the method described above in FIG. 12 to identify qualified beats for each sensing vector, Block 716, the device obtains a qualified beat, Block 718, and determines a subgroup in which to place the current identified qualified beat, Block 720. Once subgroups have been determined in response to a predetermined number of subgroups within a predetermined time period, No in Block 722, such as 15 qualified beats occurring with 60 seconds, for example, the device determines whether one of the resulting subgroups is greater than or equal to a subgroup threshold, Block 724. If one of the resulting subgroups is not greater than or equal to the subgroup threshold, No in Block 724, the process is repeated using the next predetermined number of qualified beats, Block 718. For example, according to one embodiment, the subgroup threshold may be set as 10 beats that are determined to be matched beats based on the beat-based morphology matching scheme using the normalized waveform area difference described above device.

If one of the resulting subgroups is determined to be greater than or equal to the subgroup threshold, Yes in Block 724, the template is generated using the 10 beats populating the subgroup, Block 726. According to one embodiment, the template is generated in Block 726 using the ensemble averaging, described above, of those 10 beats.

Figure 14:
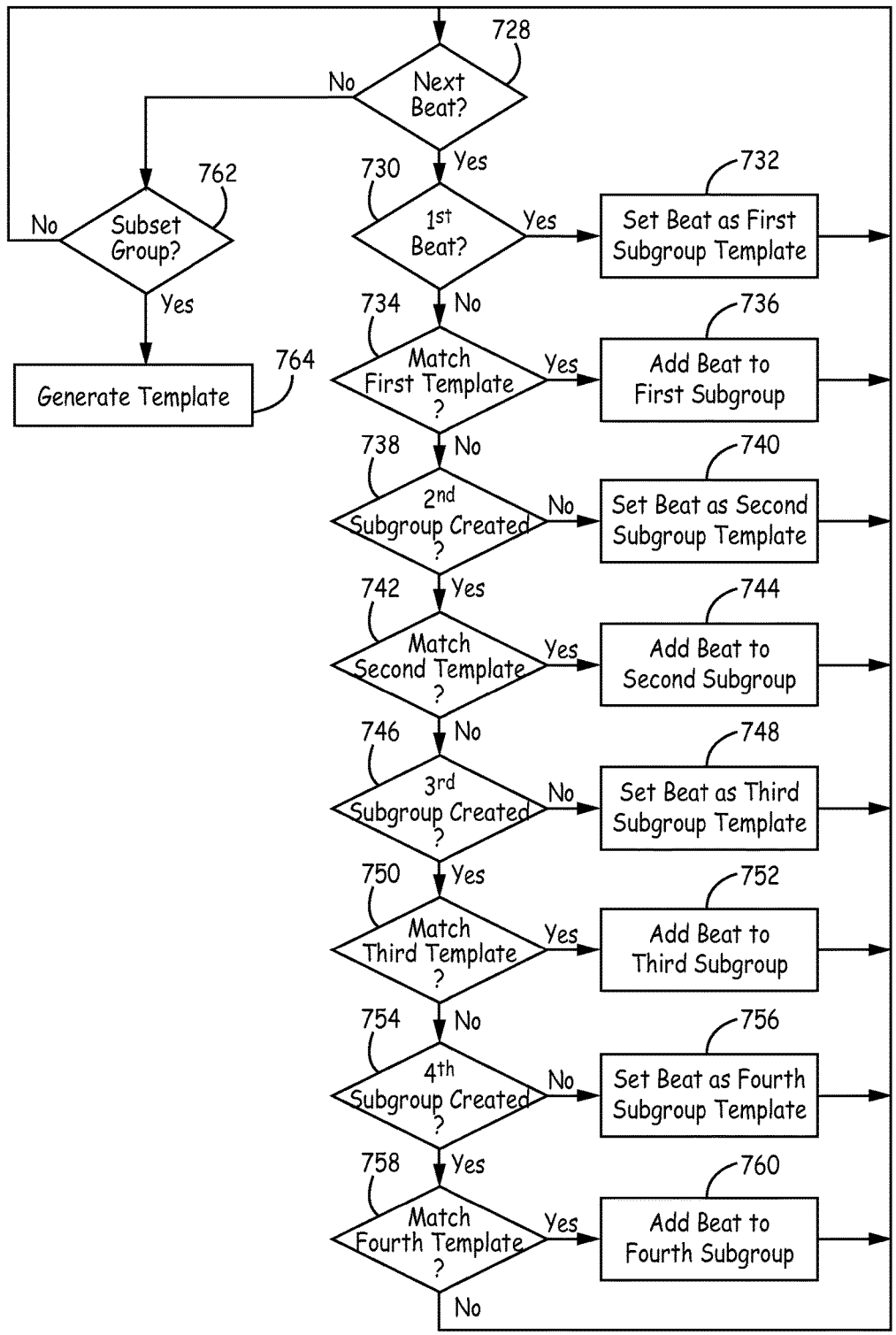
FIG. 14 is a schematic diagram of determining of subgroups for qualified beats during generation of a template, according to an embodiment of the disclosure.

FIG. 14 is a schematic diagram of determining of subgroups for qualified beats during generation of a template, according to an embodiment of the disclosure. As illustrated in FIG. 14, during placement of qualified beats within subgroups, Blocks 718-722 of FIG. 13, the first determined qualified beat, Yes in Block 730, is placed within a first subgroup, and since it is the first beat positioned within the subgroup, the beat is identified as the subgroup template beat, Block 732. The next determined qualified beat, Block 728, is then compared to the template beat of the first subgroup, Block 734, using the NWAD scheme described above. In particular, a determination is made as to whether the determined match between the second beat and the template beat of the first subgroup is greater than a predetermined match threshold, such as 60 percent for example.

If the second qualified beat matches the template beat of the first subgroup, Yes in Block 734, the beat is positioned within the first subgroup Block 736. If the second qualified beat does not match the template beat of the first subgroup, No in Block 734, a determination is made as to whether a second subset of beats has been created, Block 738. If a second subset of beats has not been created, No in Block 738, the beat is placed within a second subgroup, and since it is the first beat positioned within the second subgroup, the beat is identified as the second subgroup template beat, Block 740.

Once the second qualified beat is either placed in the first subgroup Block 736 or the second subgroup, Block 740, the third qualified beat is compared to the template beat of the first subgroup, and a determination is made as to whether the NWAD determined between the third beat and the template beat of the first subgroup is greater than the match threshold, Block 734. If the third qualified beat matches the template beat of the first subgroup, Yes in Block 734, the beat is positioned within the first subgroup, Block 736. If the third qualified beat does not match the template beat of the first subgroup, No in Block 734, the beat is compared to the template beat of the second subgroup, and a determination is made as to whether the NWAD determined between the third beat and the template beat of the second subgroup is greater than the match threshold, Block 742. If the third qualified beat matches the template beat of the second subgroup, Yes in Block 742, the beat is positioned within the second subgroup, Block 744. If the third qualified beat does not match the template beat of the second subgroup, No in Block 742, a determination is made as to whether a third subgroup has been created, Block 746. Since a third subgroup has not been created, No in Block 746, the third beat is placed within a third subgroup, and since it is the first beat positioned within the third subgroup, the beat is identified as the third subgroup template beat, Block 748.

Once the third qualified beat is either placed in the first subgroup, Block 736, the second subgroup, Block 744, or as the template beat of the third subgroup, Block 748, the fourth qualified beat, Block 728, is compared to the template beat of the first subgroup, and a determination is made as to whether the NWAD determined between the fourth beat and the template beat of the first subgroup is greater than the match threshold, Block 734. If the fourth qualified beat matches the template beat of the first subgroup, Yes in Block 734, the beat is positioned within the first subgroup, Block 736. If the fourth qualified beat does not match the template beat of the first subgroup, No in Block 734, if the second subset group was created by the second beat or the third beat, Block 740, the beat is compared to the template beat of the second subgroup, and a determination is made as to whether the NWAD determined between the fourth beat and the template beat of the second subgroup is greater than the match threshold, Block 742. If the fourth qualified beat matches the template beat of the second subgroup, Yes in Block 742, the beat is positioned within the second subgroup, Block 744.

If the fourth qualified beat does not match the template beat of the second subgroup, No in Block 742, if the third subset group was created by the third beat, Block 746, the beat is compared to the template beat of the third subgroup, and a determination is made as to whether the NWAD determined between the fourth beat and the template beat of the third subgroup is greater than the match threshold, Block 750. If the fourth qualified beat matches the template beat of the third subgroup, Yes in Block 750, the beat is positioned within the third subgroup, Block 752. If the fourth qualified beat does not match the template beat of the third subgroup, No in Block 750, a determination is made as to whether a fourth subgroup has been created, Block 754. Since a fourth subgroup has not been created, No in Block 754, the fourth beat is placed within a fourth subgroup, and since it is the first beat positioned within the fourth subgroup, the beat is identified as the third subgroup template beat, Block 756.

Once the fourth qualified beat is either placed in the first subgroup, Block 736, the second subgroup, Block 744, the third subset group, Block 752, or as the template beat of the fourth subgroup, Block 756, the device gets the fifth qualified beat, Block 728, and compares the fifth beat to the template beat of the first subgroup, and a determination is made as to whether the NWAD determined between the fourth beat and the template beat of the first subgroup is greater than the match threshold, Block 734. If the fifth qualified beat matches the template beat of the first subgroup, Yes in Block 734, the beat is positioned within the first subgroup, Block 736. If the fifth qualified beat does not match the template beat of the first subgroup, No in Block 734, if the second subset group was created by the one of the prior beats, Block 740, the fifth beat is compared to the template beat of the second subgroup, and a determination is made as to whether the NWAD determined between the fourth beat and the template beat of the second subgroup is greater than the match threshold, Block 742.

If the fifth qualified beat matches the template beat of the second subgroup, Yes in Block 742, the beat is positioned within the second subgroup, Block 744. If the fifth qualified beat does not match the template beat of the second subgroup, No in Block 742, and if the third subset group was created by one of the prior beats Block 746, the fifth beat is compared to the template beat of the third subgroup, and a determination is made as to whether the NWAD determined between the fifth beat and the template beat of the third subgroup is greater than the match threshold, Block 750. If the fifth qualified beat matches the template beat of the third subgroup, Yes in Block 750, the beat is positioned within the third subgroup, Block 752. If the fifth qualified beat does not match the template beat of the third subgroup, No in Block 750, and if the fourth subset group was created by the fourth beat, Block 756, the fifth beat is compared to the template beat of the fourth subgroup, and a determination is made as to whether the NWAD determined between the fifth beat and the template beat of the fourth subgroup is greater than the match threshold, Block 758. If the fifth qualified beat matches the template beat of the fourth subgroup, Yes in Block 758, the beat is positioned within the fourth subgroup, Block 760.

If the fifth qualified beat does not match the template beat of the fourth subgroup, No in Block 758, the beats are discarded and the process is repeated with newly obtained qualified beats. The process is continued with subsequent beats until either 15 beats have been evaluated and placed in one of the subsets, Blocks 736, 744, 752, 760, or discarded, or a timer has expired, i.e., 60 seconds for example. A determination is then made as to whether one of the subsets, Blocks 736, 744, 752 760, contains a threshold number of beats, Block 762, such as 10 beats for example. If none of the subsets contain the threshold number of beats, No in Block 762, the process is determined for the next predetermined number of beats or until the timer expires. If one of the subsets contain the threshold number of beats, Yes in Block 762, the device utilizes the 10 beats to generates a template, Block 764, by ensemble-averaging the beats, as described above, aligning the beats with the first beat in the subgroup.

In this way, the device sets the first qualified-beat as the first subgroup template (i.e., the first beat in the subgroup), and if the second qualified beat matches (NWAD>=60%) the first subgroup template beat, then, the second beat is placed in the first subgroup. If the second beat does not match the first subgroup template beat, then the second beat is placed in the second subgroup as the second subgroup template. If the third beat matches the first subgroup template beat, then the third beat is placed in the first subgroup. If the third beat does not match the first subgroup template beat and if the second subgroup template does not exist (because the second beat was placed in the first subgroup) the third beat is placed in the second subgroup as the second subgroup template. Otherwise, if the second subgroup template already exists, and the third beat matches the second subgroup template, the third beat is placed in the second subgroup, or if the third beat doesn't match the second subgroup template, then the third beat is placed in the third subgroup as the third subgroup template.

Next, if the fourth beat matches the first subgroup template, then the forth beat is placed in the first subgroup. If the fourth beat does not match the first subgroup template beat and if the second subgroup template does not exist (because the second or third beat was placed in the first subgroup) the fourth beat is placed in the second subgroup as the second subgroup template. Otherwise, if the second subgroup template already exists, and the fourth beat matches the second subgroup template, the fourth beat is placed in the second subgroup. If the fourth beat doesn't match the second subgroup template, and if the third subgroup template does not exist (because the third beat was placed in the first or second subgroup) the fourth beat is placed in the third subgroup as the third subgroup template. Otherwise if the third subgroup template already exists (because the third beat was placed in the third subgroup) and the fourth beat matches the third subgroup template, the fourth beat is placed in the third subgroup. If the fourth beat doesn't match the third subgroup template, then the fourth beat is placed in the fourth subgroup as the fourth subgroup template.

Next, if the fifth beat matches the first subgroup template, then the fifth beat is placed in the first subgroup. If the fifth beat does not match the first subgroup template, then if the second subgroup template does not exist, the fifth beat is placed in the second subgroup as the second subgroup template. Otherwise, if the second subgroup template already exists, and the fifth beat matches the second subgroup template, the fifth beat is placed in the second subgroup. If the fifth beat doesn't match the second subgroup template, then if the third subgroup template does not exist, the fifth beat is placed in the third subgroup as the third subgroup template. If the third subgroup template already exists, the fifth beat is compared to the third subgroup template, and if the fifth beat matches the third subgroup template, then the fifth beat is paced in the third subgroup. If the fifth beat matches the third subgroup template, then if the fourth subgroup template does not exist, the fifth beat is placed in the fourth subgroup as the fourth subgroup template. Otherwise, if the fourth subgroup template already exists, and the fifth beat matches the fourth subgroup template, then the fifth beat is placed in the fourth subgroup. If the fifth beat does not match the fourth subgroup template, then the fifth beat is discarded, and the acquisition process is restarted. In another embodiment, if the fifth beat does not match the fourth subgroup template, the fifth beat may merely be discarded and the process repeated with the next beat until 15 beats have been analyzed or the timer has expired.

Assuming beats 1-5 are placed in one of the four subgroups, the process is repeated for beats 6-15 until one of the subgroups is populated with ten beats, and the ten beats are then used in the ensemble averaging scheme to generate a template, as described above, by aligning the last nine beats with the first beat, using the alignment process described above, for example, to build the template.

It is understood that while the features in the above described flowcharts are described as being performed in a certain sequence, the order in performing the features of the flow charts may be different from the order described. Thus, a method and apparatus for beat acquisition during template generation have been presented in the foregoing description with reference to specific embodiments. It is appreciated that various modifications to the referenced embodiments may be made without departing from the scope of the disclosure as set forth in the following claims.

I claim:

1. A medical device for generating a template, comprising:
   a plurality of electrodes configured to sense a cardiac signal;
   a storage device comprising a plurality of subgroups for storing beats; and
   a processor configured to:
      identify a plurality of beats in the sensed cardiac signal,
      determine that a first beat of the plurality of beats is an initial beat to be stored in the first subgroup of the plurality of subgroups,
      set the first beat as a first subgroup template beat in response to the first beat being the initial beat,
      determine, for each remaining beat of the plurality of beats, whether to store the beat within a subgroup of the plurality of subgroups of the storage device,
      determine whether a number of beats stored in one of the plurality of subgroups exceeds a subgroup threshold, and in response to the number of beats stored in the one of the plurality of subgroups exceeding the subgroup threshold, and
      generate a template beat using one or more beats of the one of the plurality of subgroups that exceeds the subgroup threshold.

2. The medical device of claim 1, wherein the processor is configured to compare a second beat of the plurality of beats to the first subgroup template beat and determine a match between the second beat and the first subgroup template beat, determine whether the match is greater than a match threshold, and store the second beat within the first subgroup in response to the match being greater than the match threshold.

3. The medical device of claim 2, wherein the processor is configured to determine, in response to the match not being greater than the match threshold, whether a second subgroup has been created, create a second subgroup in response to a second subgroup having not been created, and set the second beat as a second subgroup template beat.

4. The medical device of claim 3, wherein the processor is configured to compare the second beat to a second subgroup template beat of the second subgroup in response to a second subgroup having been created, determine a match between the second beat and the second subgroup template beat, determine whether the match between the second beat and the second subgroup template beat is greater than the match threshold, and store the second beat within the second subgroup in response to the match between the second beat and the second subgroup template beat being greater than the match threshold.

5. The medical device of claim 2, wherein the processor is configured to compare the second beat to a second subgroup template beat of a second subgroup and determine a match between the second beat and the second subgroup template beat in response to the match between the second beat and the first subgroup template beat not being greater than the match threshold, determine whether the match between the second beat and the second subgroup template beat is greater than the match threshold, and store the second beat within the second subgroup in response to the match between the second beat and the second subgroup template beat being greater than the match threshold.

6. The medical device of claim 1, wherein the plurality of beats comprises 15 beats and the subgroup threshold comprises 10 beats.

7. The medical device of claim 6, wherein the plurality of subgroups comprises 4 subgroups.

8. The medical device of claim 1, wherein the plurality of beats is a first plurality of beats, and wherein the processor is further configured to identify a next plurality of beats in the sensed cardiac signal, in response to the number of beats stored in each of the plurality of subgroups not exceeding the subgroup threshold, determine, for each of the next plurality of beats, whether to store the beat within the one of the plurality of subgroups, determine whether a number of beats of the next plurality of beats stored in the one of the plurality of subgroups exceeds the subgroup threshold, and generate the template beat using one or more of the beats of the next plurality of beats stored in the one of the plurality of subgroups that exceeds the subgroup threshold.

9. The medical device of claim 1, wherein the plurality of electrodes form a first sensing vector sensing a first interval of the cardiac signal during a predetermined time period and a second sensing vector simultaneously sensing a second interval of the cardiac signal during the predetermined time period, and wherein the processor is configured to determine interval conditions based on the first interval and the second interval, and determine whether to identify the first interval and the second interval as qualified intervals for generating a template based on the determined intervals conditions.

10. A subcutaneous cardiac device for generating a template, comprising:
    a plurality of electrodes configured to sense a cardiac signal;
    a storage device;
    a processor configured to:
        identify a plurality of beats in the sensed cardiac signal,
        determine that a first beat of the plurality of beats is an initial beat to be stored in the first subgroup of the plurality of subgroups,
        set the first beat as a first subgroup template beat in response to the first beat being the initial beat,
        determine, for each remaining beat of the plurality of beats, whether to store the beat within a subgroup of a plurality of subgroups of the storage device,
        determine whether a number of beats stored in one of the plurality of subgroups exceeds a subgroup threshold,
        generate a template beat in response to the number of beats stored in the one of the plurality of subgroups exceeding the subgroup threshold using one or more beats stored in the one of the plurality of subgroups that exceeds the subgroup threshold,
        and
        detect a cardiac event based at least on a comparison of beats subsequent the plurality of beats to the generated template beat; and
    a high voltage output circuit to deliver therapy via electrodes of the plurality of electrodes in response to the processor detecting the cardiac event.

11. The subcutaneous cardiac device of claim 10, wherein the processor is configured to compare a second beat of the plurality of beats to the first subgroup template beat and determine a match between the second beat and the first subgroup template beat, determine whether the match is greater than a match threshold, and store the second beat within the first subgroup in response to the match being greater than the match threshold.

12. The subcutaneous cardiac device of claim 11, wherein the processor is configured to determine, in response to the match not being greater than the match threshold, whether a second subgroup has been created, and set the second beat as a second subgroup template beat in response to a second beat subgroup not being created.

13. The subcutaneous cardiac device of claim 12, wherein the processor is configured to compare the second beat to a second subgroup template beat of the second subgroup in response to a second subgroup being created, determine a match between the second beat and the second subgroup template beat, determine whether the match between the second beat and the second subgroup template beat is greater than the match threshold, and store the second beat within the second subgroup in response to the match between the second beat and the second subgroup template beat being greater than the match threshold.

14. The subcutaneous cardiac device of claim 11, wherein the processor is configured to compare the second beat to a second subgroup template beat of a second subgroup and determine a match between the second beat and the second subgroup template beat in response to the match between the second beat and the first subgroup template beat not being greater than the match threshold, determine whether the match between the second beat and the second subgroup template beat is greater than the match threshold, and store the second beat within the second subgroup in response to the match between the second beat and the second subgroup template beat being greater than the match threshold.

15. The subcutaneous cardiac device of claim 10, wherein the plurality of beats is a first plurality of beats, and wherein the processor is further configured to identify a next plurality of beats in the sensed cardiac signal in response to the number of beats stored in the one of the plurality of subgroups not exceeding the subgroup threshold, determine, for each of the next plurality of beats, whether to store the beat within the one of the plurality of subgroups, determine whether a number of beats of the next plurality of beats stored in the one of the plurality of subgroups exceeds the subgroup threshold, and generate the template beat using one or more of the beats of the next plurality of beats stored the in one of the plurality of subgroups that exceeds the subgroup threshold.

16. The medical device of claim 1, wherein the processor is configured to generate the template beat by averaging the beats stored within the one of the plurality of subgroups that exceeds the subgroup threshold.

17. The medical device of claim 1, wherein the processor is further configured to:
    detect a cardiac event based at least on a comparison of beats subsequent the plurality of beats to the generated template beat; and
    control the medical device to deliver a therapy in response to the detection of the cardiac event.

18. The medical device of claim 17, further comprising a high voltage output circuit to deliver the therapy, wherein the therapy comprises an anti-tachyarrhythmia shock.

19. The medical device of claim 1, wherein the plurality of beats is a first plurality of beats, and wherein the processor is configured to, for each of the plurality of subgroups, compare a beat of the first plurality of beats to a respective subgroup template beat and determine a match between the beat and the subgroup template beat, determine whether the match is greater than a match threshold, and, in response to determining that the match is not greater than a match threshold for each of the plurality of subgroup template beats, discard the first plurality of beats and identify a second plurality of beats in the sensed cardiac signal,
    wherein the processor is configured to determine, for each of the next plurality of beats, whether to store the beat within the one of the plurality of subgroups, determine whether a number of beats of the next plurality of beats stored in the one of the plurality of subgroups exceeds the subgroup threshold, and generate the template beat using one or more of the beats of the next plurality of beats stored in the one of the plurality of subgroups that exceeds the subgroup threshold.

20. The subcutaneous cardiac device of claim 10, wherein the plurality of beats is a first plurality of beats, and wherein the processor is configured to, for each of the plurality of subgroups, compare a beat of the first plurality of beats to a respective subgroup template beat and determine a match between the beat and the subgroup template beat, determine whether the match is greater than a match threshold, and, in response to determining that the match is not greater than a match threshold for each of the plurality of subgroup template beats, discard the first plurality of beats and identify a second plurality of beats in the sensed cardiac signal, wherein the processor is configured to determine, for each of the next plurality of beats, whether to store the beat within the one of the plurality of subgroups, determine whether a number of beats of the next plurality of beats stored in the one of the plurality of subgroups exceeds the subgroup threshold, and generate the template beat using one or more of the beats of the next plurality of beats stored in the one of the plurality of subgroups that exceeds the subgroup threshold.

\* \* \* \* \*